(12) United States Patent
Sugiura et al.

(10) Patent No.: US 8,129,148 B2
(45) Date of Patent: Mar. 6, 2012

(54) PROCESS FOR PREPARATION OF CHONDROITIN FRACTION

(75) Inventors: Nobuo Sugiura, Aichi (JP); Koji Kimata, Aichi (JP)

(73) Assignee: Seikagaku Corporation, Chiyoda-ku, Tokyo (JP)

( * ) Notice: Subject to any disclaimer, the term of this patent is extended or adjusted under 35 U.S.C. 154(b) by 948 days.

(21) Appl. No.: 12/064,810

(22) PCT Filed: Aug. 23, 2006

(86) PCT No.: PCT/JP2006/316523
§ 371 (c)(1),
(2), (4) Date: Feb. 25, 2008

(87) PCT Pub. No.: WO2007/023867
PCT Pub. Date: Mar. 1, 2007

(65) Prior Publication Data
US 2009/0155851 A1 Jun. 18, 2009

(30) Foreign Application Priority Data

Aug. 24, 2005 (JP) ................. 2005-242272
Jul. 27, 2006 (JP) ................. 2006-205427

(51) Int. Cl.
*C12P 19/28* (2006.01)
(52) U.S. Cl. ....... 435/85; 435/84; 435/252.33; 435/170; 536/18.7
(58) Field of Classification Search .................... 435/84, 435/85; 536/18.7
See application file for complete search history.

(56) References Cited

U.S. PATENT DOCUMENTS

| | | | |
|---|---|---|---|
| 2003/0109693 A1 | 6/2003 | Ninomiya et al. | |
| 2006/0052335 A1 | 3/2006 | Narimatsu et al. | |
| 2006/0057697 A1 | 3/2006 | Narimatsu et al. | |

FOREIGN PATENT DOCUMENTS

| | | |
|---|---|---|
| JP | 2004-166702 | 6/2004 |
| WO | WO 00/27437 | 5/2000 |

OTHER PUBLICATIONS

Sugiura et al. Anal. Biochem. (2007) 365: 62-73.*
Ninomiya, et al. "Molecular Cloning and Characterization of Chondroitin Polymerase from *Escherichia coli* Strain K4," *J. Biol. Chem.*, vol. 277, No. 24, pp. 21567-21575, 2002.
Gotoh, et al. Molecular Cloning and Characterization of a Novel Chondroitin Sulfate Glucuronyltransferase that Transfers Glucuronic Acid to N-Acetylgalactosamine, *J. Biol. Chem.*, vol. 277, No. 41, pp. 38179-38188, 2002.
Sugiura, "Tosa Gosei Koso o Riyo Shita Iryoyo Tosa No Sosei (Preparation of Saccharides for Medical Usage by Sugar Chain Synthetic Enzymes)," Dai 26 Kai The Japanese Society of Carbohydrate Research, pp. 14-15, Jul. 28, 2006.
Shimokata, et al. "Chondroitin Gosei Koso Koteika Rearctor Ni Yoru Chondroitin Oligosaccharide Chain No Chikuji Gosei (One-by-One Synthesis of Chondroitin Oligosaccharides by Chondroitin Polymerase-Immobilized Reactors)," Dai 26 Kai The Japanese Society of Carbohydrate Research Nenkai Yoshishu, p. 106, Jul. 28, 2006.
International Search Report dated Nov. 14, 2006.

* cited by examiner

*Primary Examiner* — Susan Hanley
(74) *Attorney, Agent, or Firm* — Knobbe, Martens, Olson & Bear, LLP

(57) ABSTRACT

Provided are a method for producing a fraction containing more than 50% of CH represented by the general formula (1), which comprises at least the step of allowing a glucuronic acid donor, an N-acetylgalactosamine donor, a saccharide receptor, a chondroitin polymerase derived from the *Escherichia coli* K4 strain, and $Mn^{2+}$ at a final concentration of 0.02 to 100 mM to coexist, and performing a reaction thereof under conditions of 20 to 40° C. and pH 6 to 8 for 0.5 minutes to 4 hours, and a method for producing a fraction containing more than 50% of CH represented by the general formula (2), which comprises at least the step of performing the reaction under same conditions for 10 hours or longer, which enable industrial scale production of a CH fraction of a controlled even number saccharide and odd number saccharide content ratio by a simple procedure at a low cost.

$$(GlcA\text{-}GalNAc)_n \qquad (1)$$

$$GalNAc\text{-}(GlcA\text{-}GalNAc)_n \qquad (2)$$

(In the formula, GlcA represents a glucuronic acid residue, GalNCAc represents a N-acetylgalactosamine residue, - represents a glycosidic bond, and n represents an arbitrary integer.)

2 Claims, 14 Drawing Sheets

PROCESS FOR PREPARATION OF CHONDROITIN FRACTION

CROSS-REFERENCE TO RELATED APPLICATIONS

This application is the U.S. National Phase under 35 U.S.C. §371 of International Application PCT/JP2006/316523, filed Aug. 23, 2006, which was published in a non-English language, which claims priority to JP Application No. 2005-242272, filed Aug. 24, 2005 and JP Application No. 2006-205427, filed Jul. 27, 2006.

STATEMENT REGARDING FEDERALLY SPONSORED R&D

Not applicable

PARTIES OF JOINT RESEARCH AGREEMENT

Not applicable

REFERENCE TO SEQUENCE LISTING, TABLE, OR COMPUTER PROGRAM LISTING

Not applicable

BACKGROUND OF THE INVENTION

1. Field of the Invention

The present invention relates to methods for producing a fraction of an even number saccharide or odd number saccharide having a chondroitin structure.

2. Description of the Related Art

The abbreviations used in the present specification are mentioned first.
CH: Chondroitin
CS: Chondroitin sulfate
GlcA: Glucuronic acid
GalNAc: N-Acetylgalactosamine
HA: Hyaluronic acid
K4CP: Chondroitin polymerase derived from the *Escherichia coli* K4 strain
MALDI-TOF-MS: Matrix assisted laser desorption/ionization time of flight mass spectrometry
UDP: Uridine-5'-diphosphate CH is one type of glycosaminoglycans, which comprises GlcA and GalNAc residues alternately and linearly linked with β1-3 linkages and β1-4 linkages. CH exists in cartilages and many of connective tissues in animal living bodies as chondroitin sulfate proteoglycans, and plays important roles in cell adhesion, development, differentiation, nerve cell extension, chondrogenesis and osteogenesis, anagenesis, and so forth. CS is marketed as a substance useful for drugs, health food, and so forth.

The reducing end of CH is usually bound to a core protein of a proteoglycan, and repetition disaccharide units of GlcA-GalNAc are linked to a serine residue in the protein via the so-called linkage region tetrasaccharide consisting of xylose-galactose-galactose-GlcA. However, the non-reducing end thereof has not been identified yet. Although commercially available CS is considered to have a GalNAc residue as the reducing end and a GlcA residue as the non-reducing end in many cases with acid treatment, enzyme treatment and so forth used for the production thereof, the non-reducing end may differ depending on production lots, and the present situation is that products containing CS molecules having different structures of non-reducing ends are marketed.

Although an animal-derived CH polymerase has been cloned, this enzyme itself has no CH synthesis activity, and even if the activity is exhibited, the activity is weak. Therefore, it is not sufficient for efficient industrial production of CH saccharide chain. Further, K4CP has also been cloned, and it is known that this enzyme shows a CH synthesis activity by itself, and CH can be efficiently produced by using this enzyme (Patent document 1, Non-patent document 1). However, control of the non-reducing end saccharide residue of CH, control of content ratio of even number saccharides and odd number saccharides in a product, and so forth with use of K4CP have not been described nor suggested.

Patent document 1: Japanese Patent Laid-open Publication (KOKAI) No. 2003-199583
Non-patent document 1: Ninomiya, T. et al., 2002, Journal of Biological Chemistry, Vol. 277, No. 24, pp. 21567-21575

BRIEF SUMMARY OF THE INVENTION

Object to be Solved by the Invention

An object of the present invention is to provide a method for producing a CH fraction in which content ratio of even number saccharides (CH having a GlcA residue as the non-reducing end saccharide residue) and odd number saccharides (CH having a GalNAc residue as the non-reducing end saccharide residue) is controlled, in a simple manner and at a low cost in an industrial scale by controlling the non-reducing end saccharide residues in CH in a synthetic process with a very simple method.

Means for Achieving the Object

The inventors of the present invention assiduously studied in order to achieve the aforementioned object. As a result, they found that by using K4CP and controlling the enzyme reaction time, a CH fraction containing CH molecules having either a GlcA residue or a GalNAc residue as the non-reducing end saccharide residue in a larger amount could be produced, and that by controlling concentration of $Mn^{2+}$ in the reaction, a CH fraction containing CH molecules having GlcA residues and GalNAc residues as the non-reducing ends in substantially the same amounts could be produced, and thus accomplished the present invention.

That is, the present invention provides a method for producing a fraction containing more than 500 of CH represented by the general formula (1), which comprises at least the step of allowing a GlcA donor, a GalNAC donor, a saccharide acceptor, K4CP, and $Mn^{2+}$ at a final concentration of 0.02 to 100 mM to coexist, and performing a reaction thereof under conditions of 20 to 40° C. and pH 6 to 8 for 0.5 minutes to 4 hours (henceforth referred to as the "first method of the present invention").

$$(GlcA-GalNAc)_n \qquad (1)$$

(In the formula, - represents a glycosidic bond, and n represents an arbitrary integer)

Especially, the aforementioned reaction is preferably performed under conditions of 22 to 37° C. and pH 6.2 to 7.8 for 10 minutes to 3 hours, more preferably performed under conditions of 24 to 35° C. and pH 6.5 to 7.8 for 10 minutes to 2 hours, still more preferably performed under conditions of 26 to 35° C. and pH 6.8 to 7.6 for 10 minutes to 2 hours, further preferably performed under conditions of 28 to 32° C.

and pH 7 to 7.5 for 10 minutes to 2 hours, particularly preferably performed under conditions of 28 to 32° C. and pH 7 to 7.5 for 10 minutes to 1 hour.

Above all, the aforementioned reaction is preferably performed under conditions of 20 to 37° C. and pH 6 to 8 for 0.5 to 4 hours, more preferably performed under conditions of 22 to 37° C. and pH 6.2 to 7.8 for 0.5 to 3 hours, still more preferably performed under conditions of 24 to 35° C. and pH 6.5 to 7.8 for 0.5 to 2 hours, further preferably performed under conditions of 26 to 35° C. and pH 6.8 to 7.6 for 0.5 to 2 hours, much more preferably performed under conditions of 28 to 32° C. and pH 7 to 7.5 for 0.5 to 2 hours, particularly preferably performed under conditions of 28 to 32° C. and pH 7 to 7.5 for 0.5 to 1 hour.

Further, the $Mn^{2+}$ concentration is preferably 0.02 to 35 mM, more preferably 0.2 to 35 mM, under the aforementioned conditions.

In particular, the concentration is preferably 5 to 35 mM, more preferably 10 to 30 mM, still more preferably 15 to 25 mM, particularly preferably 20 mM.

The present invention also provides a method for producing a fraction containing more than 50% of CH represented by the general formula (1), which comprises at least the step of allowing a GlcA donor, a GalNAc donor, a saccharide acceptor, K4CP, and $Mn^{2+}$ at a final concentration of 0.02 to 100 mM to coexist, and performing a reaction thereof so that all of the following conditions 1 to 3 should be satisfied (henceforth referred to as the "second method of the present invention").

(GlcA-GalNAc)$_n$ (1)

GalNAc-(GlcA-GalNAc)$_n$ (2)

(In the formulas, - represents a glycosidic bond, and n represents an arbitrary integer)
(Conditions)

Condition 1: A CH content ratio of a fraction produced by allowing the GlcA donor, the GalNAc donor, the saccharide acceptor, K4CP, and $Mn^{2+}$ at a final concentration of 0.02 to 100 mM to coexist, and performing a reaction thereof under conditions of 30° C. and pH 7.2 for 5 hours is defined to be X. The "CH content ratio" means a ratio of "molecular number of the CH represented by the general formula (1) "/" molecular number of the CH represented by the general formula (2)".

Condition 2: A reaction time providing the CH content ratio of X in a fraction produced by performing the reaction under conditions of "arbitrary temperature and pH at which K4CP can act" instead of "30° C. and pH 7.2" of the condition 1 is defined to be Y.

Condition 3: The reaction is performed at the same temperature and pH as those of the condition 2 for a time shorter than Y.

The present invention also provides a method for producing a fraction containing more than 50% of CH represented by the general formula (2), which comprises at least the step of allowing a GlcA donor, a GalNAc donor, a saccharide acceptor, K4CP, and $Mn^{2+}$ at a final concentration of 5 to 100 mM to coexist, and performing a reaction thereof under conditions of 20 to 40° C. and pH 6 to 8 for 10 hours or longer (henceforth referred to as the "third method of the present invention").

GalNAc-(GlcA-GalNAc)$_n$ (2)

(In the formula, - represents a glycosidic bond, and n represents an arbitrary integer)

Especially, the aforementioned reaction is preferably performed under conditions of 22 to 37° C. and pH 6.2 to 7.8 for 10 to 30 hours, more preferably performed under conditions of 24 to 35° C. and pH 6.5 to 7.8 for 12 to 24 hours, still more preferably performed under conditions of 26 to 35° C. and pH 6.8 to 7.6 for 12 to 24 hours, further preferably performed under conditions of 28 to 32° C. and pH 7 to 7.5 for 12 to 24 hours, particularly preferably performed under conditions of 28 to 32° C. and pH 7 to 7.5 for 15 to 20 hours.

Further, the $Mn^{2+}$ concentration is preferably 5 to 35 mM, more preferably 10 to 30 mM, still more preferably 15 to 25 mM, particularly preferably 20 mM, under the aforementioned conditions.

The present invention also provides a method for producing a fraction containing more than 50% of CH represented by the general formula (2), which comprises at least the step of allowing a GlcA donor, a GalNAc donor, a saccharide acceptor, K4CP, and $Mn^{2+}$ at a final concentration of 5 to 100 mM to coexist, and performing a reaction thereof so that all of the following conditions 4 to 6 should be satisfied (henceforth referred to as the "fourth method of the present invention").

(GlcA-GalNAc)$_n$ (1)

GalNAc-(GlcA-GalNAc)$_n$ (2)

(In the formulas, - represents a glycosidic bond, and n represents an arbitrary integer)
(Conditions)

Condition 4: A CH content ratio of a fraction produced by allowing the GlcA donor, the GalNAc donor, the saccharide acceptor, K4CP, and $Mn^{2+}$ at a final concentration of 5 to 100 mM to coexist, and performing a reaction thereof under conditions of 30° C. and pH 7.2 for 8 hours is defined to be X. The "CH content ratio" means a ratio of "molecular number of the CH represented by the general formula (1) "/" molecular number of the CH represented by the general formula (2)".

Conditions 5: A reaction time providing the CH content ratio of X in a fraction produced by performing the reaction under conditions of "arbitrary temperature and pH at which K4CP can act" instead of "30° C. and pH 7.2" of the condition 4 is defined to be Y.

Condition 6: The reaction is performed at the same temperature and pH as those of the condition 5 for a time longer than Y.

The present invention also provides a method for producing a fraction containing substantially 1000 of CH represented by the general formula (1), which comprises at least the step of allowing a GlcA donor, a saccharide acceptor, K4CP, and $Mn^{2+}$ at a final concentration of 0.02 to 100 mM to coexist, and performing a reaction thereof so that all of the following conditions A to C should be satisfied (henceforth referred to as the "fifth method of the present invention").

(GlcA-GalNAc)$_n$ (1)

GalNAc-(GlcA-GalNAc)$_n$ (2)

(In the formulas, - represents a glycosidic bond, and n represents an arbitrary integer)
(Conditions)
Condition A: A CH content ratio of a fraction produced by allowing the GlcA donor, the saccharide acceptor, K4CP, and $Mn^{2+}$ at a final concentration of 0.02 to 100 mM to coexist, and performing a reaction thereof under conditions of 30° C. and pH 7.2 for 0.5 hour is defined to be X. The "CH content ratio" means a ratio of "molecular number of the CH represented by the general formula (1) "/" molecular number of the CH represented by the general formula (2)":
Conditions B: A reaction time providing the CH content ratio of X in a fraction produced when the reaction is performed under conditions of "arbitrary temperature and pH at which K4CP can act" instead of "30° C. and pH 7.2" of the condition A is defined to be Y.

Condition C: The reaction is performed at the same temperature and pH as those of the condition B for a time longer than Y.

The present invention also provides a method for producing a fraction containing substantially 100% of CH represented by the general formula (2), which comprises at least the step of allowing a GalNAc donor, a saccharide acceptor, K4CP, and $Mn^{2+}$ at a final concentration of 0.02 to 100 mM to coexist, and performing a reaction thereof so that all of the following conditions D to F should be satisfied (henceforth referred to as the "sixth method of the present invention").

(GlcA-GalNAc)$_n$ (1)

GalNAc-(GlcA-GalNAc)$_n$ (2)

(In the formulas, - represents a glycosidic bond, and n represents an arbitrary integer)
(Conditions)
Condition D: A CH content ratio of a fraction produced by allowing the GalNAc donor, the saccharide acceptor, K4CP, and $Mn^{2+}$ at a final concentration of 0.02 to 100 mM to coexist, and performing a reaction thereof under conditions of 30° C. and pH 7.2 for 0.5 hour is defined to be X. The "CH content ratio" mentioned above means a ratio of "molecular number of the CH represented by the general formula (1) "/" molecular number of the CH represented by the general formula (2)".
Conditions E: A reaction time providing the CH content ratio of X in a fraction produced when the reaction is performed under conditions of "arbitrary temperature and pH at which K4CP can act" instead of "30° C. and pH 7.2" of the condition D is defined to be Y.
Condition F: The reaction is performed at the same temperature and pH as those of the condition E for a time longer than Y.

The present invention also provides a method for producing a fraction containing CH represented by the general formulas (1) and (2) at a content ratio ((1):(2)) of 45:55 to 55:45, which comprises at least the step of allowing a GlcA donor, a GalNAc donor, a saccharide acceptor, K4CP, and $Mn^{2+}$ at a final concentration of 0.02 to 2 mM to coexist, and performing a reaction thereof under conditions of 20 to 40° C. and pH 6 to 8 for 5 hours or longer (henceforth referred to as the "seventh method of the present invention").

(GlcA-GalNAc)$_n$ (1)

GalNAc-(GlcA-GalNAc)$_n$ (2)

(In the formulas, - represents a glycosidic bond, and n represents an arbitrary integer)
Especially, the aforementioned reaction is preferably performed under conditions of 22 to 37° C. and pH 6.2 to 7.8 for 10 to 30 hours, more preferably performed under conditions of 24 to 35° C. and pH 6.5 to 7.8 for 12 to 24 hours, still more preferably performed under conditions of 26 to 35° C. and pH 6.8 to 7.6 for 12 to 24 hours, further preferably performed under conditions of 28 to 32° C. and pH 7 to 7.5 for 12 to 24 hours, particularly preferably performed under conditions of 28 to 32° C. and pH 7 to 7.5 for 15 to 18 hours.

Further, the $Mn^{2+}$ concentration is preferably 0.1 to 1 mM, more preferably 0.2 mM, under the aforementioned conditions.

The present invention also provides a method for producing a fraction containing CH represented by the general formulas (1) and (2) at a desired content ratio, which comprises at least the step of allowing a GlcA donor and/or a GalNAc donor, a saccharide acceptor, K4CP, and $Mn^{2+}$ to coexist, and performing a reaction thereof under conditions of 20 to 40° C. and pH 6 to 8 (henceforth referred to as the "eighth method of the present invention").

(GlcA-GalNAc)$_n$ (1)

GalNAc-(GlcA-GalNAc)$_n$ (2)

(In the formulas, - represents a glycosidic bond, and n represents an arbitrary integer)
The first to eighth methods of the present invention are henceforth collectively referred to simply as the "method of the present invention".

Effect of the Invention

Since a CH fraction containing either even number saccharides (CH having a GlcA residue as the non-reducing end saccharide residue) or odd number saccharides (CH having a GalNAc residue as the non-reducing end saccharide residue) in an amount larger than that of the other, a CH fraction containing even number saccharides and odd number saccharides in equivalent amounts, and a CH fraction containing even number saccharides and odd number saccharides in a desired content ratio can be produced by the method of the present invention in a simple manner and at a low cost in an industrial scale, the method of the present invention is very useful.

Saccharide chains of CH having different reducing end saccharides, in a fraction produced by the method of the present invention are expected to show different reactivities to modification such as that of a sulfate group transferase, or different physiological activities. Therefore, they are useful for the manufacture of drugs. The method of the present invention that enables production of a CH fraction predominantly containing CH molecules having specific reducing end saccharides or a CH fraction containing CH molecules having different reducing end saccharides at a desired ratio can be utilized for the manufacture of drugs and so forth.

BRIEF DESCRIPTION OF THE DRAWINGS

FIG. 14(A) shows the results of MALDI-TOF-MS analysis of the fraction obtained in the elution time from 17 to 18 minutes. FIG. 14(B) shows the results of MALDI-TOF-MS analysis of the fraction obtained in the elution time from 15 to 16 minutes.

DETAILED DESCRIPTION OF THE INVENTION

Figure 1:
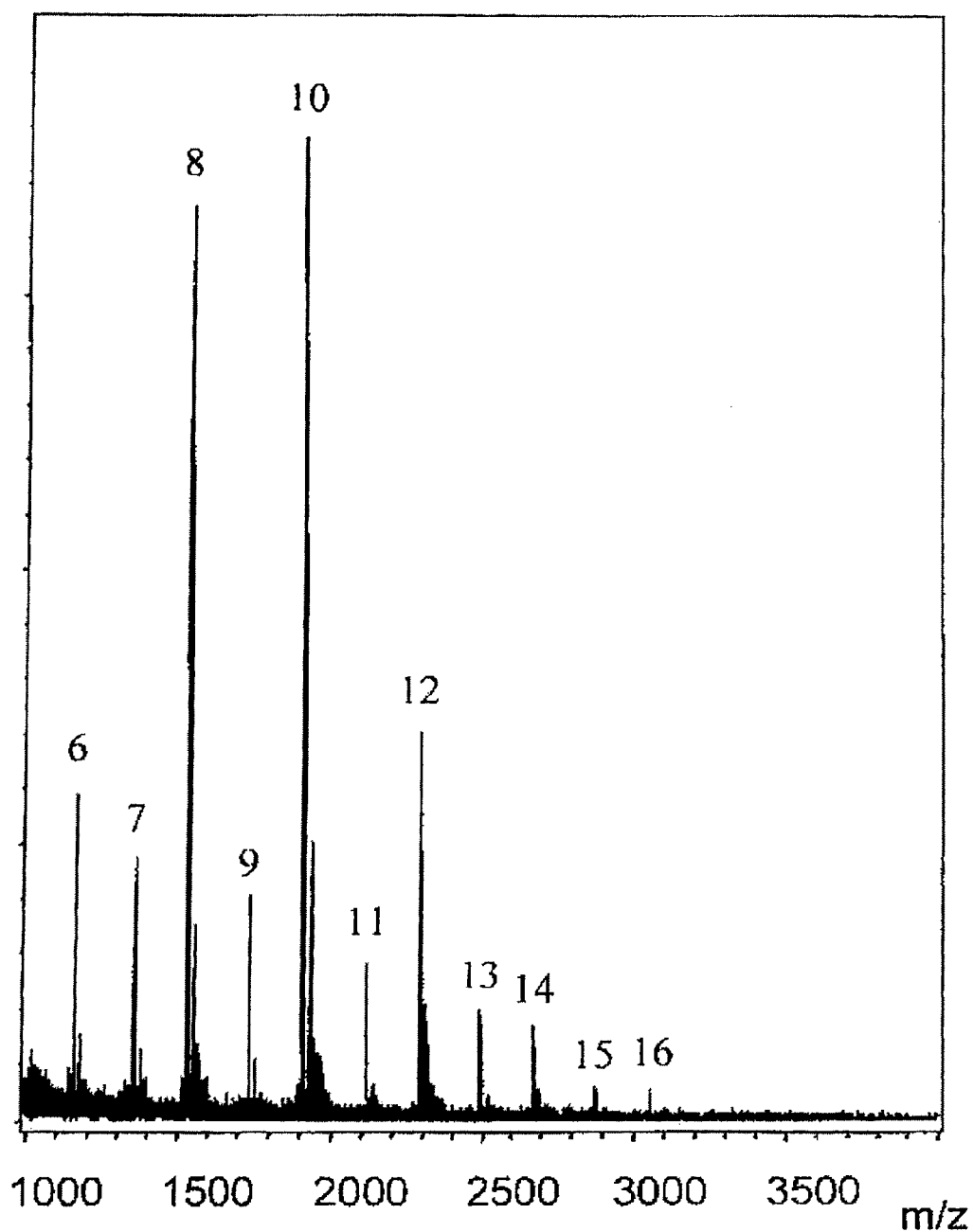
FIG. 1 MALDI-TOF-MS spectrum of a product obtained after the reaction for 0.5 hour.

Hereafter, the present invention will be explained in detail with reference to the best modes for carrying out the invention. The symbol "%" mentioned in this specification and the claims means "mole %" unless specifically indicated. Further, the various characteristics mentioned in this specification and the claims were determined by the analytical methods described in the examples of this specification unless specifically indicated.

Hereafter, the first to eighth methods of the present invention will be explained, respectively.

<1> First Method of the Present Invention

The first method of the present invention is a method for producing a fraction containing more than 50% of CH represented by the general formula (1), which comprises at least the step of allowing a GlcA donor, a GalNAC donor, a saccharide acceptor, K4CP, and $Mn^{2+}$ at a final concentration of 0.02 to 100 mM to coexist, and performing a reaction thereof under conditions of 20 to 40° C. and pH 6 to 8 for 0.5 minutes to 4 hours.

$$(\text{GlcA-GalNAc})_n \tag{1}$$

(In the formula, - represents a glycosidic bond, and n represents an arbitrary integer (in this specification, "integer" means a positive integer))

Although the "GlcA donor" used in the method of the present invention is not limited so long as it is a molecule having an ability to supply a GlcA residue to a certain saccharide chain molecule, a GlcA nucleotide is preferred. Examples of the GlcA nucleotide include UDP-GlcA, dTDP (deoxythymidine-5'-diphosphate)-GlcA and so forth, and UDP-GlcA is preferred.

Although the "GalNAc donor" used in the method of the present invention is not limited so long as it is a molecule having an ability to supply a GalNAc residue to a certain saccharide chain molecule, a GalNAc nucleotide is preferred. Examples of the GalNAc nucleotide include UDP-GalNAc, dTDP (deoxythymidine-5'-diphosphate)-GalNAc and so forth, and UDP-GalNAc is preferred.

These sugar nucleotides may be produced by known methods, or commercial products may be used.

The "saccharide acceptor" used in the method of the present invention is not limited so long as it is a saccharide chain represented by the general formula (3) or (4).

$$\text{GlcA-GalNAc-R}^1 \tag{3}$$

$$\text{GalNAc-GlcA-R}^2 \tag{4}$$

(In the formulas, - represents a glycosidic bond, and $R^1$ and $R^2$ represent arbitrary groups, which may be the same or different)

Examples of "$R^1$" and "$R^2$" include a residue of a saccharide chain having CH structure, a residue of a saccharide chain having HA structure, and so forth. Examples of the residue of a saccharide chain having CH structure include a CH residue, a CS residue, and so forth. The size thereof is not also particularly limited.

As sources of $R^1$ and $R^2$ in the saccharide acceptor represented by the general formula (3) or (4), a wide range of compounds can be used, specifically, from CH oligosaccharides such as CH disaccharide, CH trisaccharide, CH tetrasaccharide, CH pentasaccharide, CH hexasaccharide, CH heptasaccharide, CH octasaccharide, CH nonasaccharide and CH decasaccharide to CH polymers, from CS oligosaccharides such as CS disaccharide, CS trisaccharide, CS tetrasaccharide, CS pentasaccharide, CS hexasaccharide, CS heptasaccharide, CS octasaccharide, CS nonasaccharide and CS decasaccharide to CS polymers, and from HA oligosaccharides such as HA disaccharide, HA trisaccharide, HA tetrasaccharide, HA pentasaccharide, HA hexasaccharide, HA heptasaccharide, HA octasaccharide, HA nonasaccharide and HA decasaccharide to HA polymers.

These saccharide acceptors may be produced by known methods, or commercial products may also be used.

CH represented by the general formula (1) or (2) in the fraction produced by the method of the present invention also includes a CH molecule having $R^1$ or $R^2$ originating in the aforementioned saccharide acceptor at the end of the chain.

"$Mn^{2+}$" used in the method of the present invention is not particularly limited so long as it exists as $Mn^{2+}$ in a solution and does not inhibit the reaction catalyzed by K4CP, and for example, $MnCl_2$ can be used.

"K4CP" used in the method of the present invention can be obtained by the methods described in Non-patent document 1 and Patent document 1 mentioned above. This K4CP is a polymerase which extends CH by catalyzing a reaction of CH as an acceptor substrate, a GalNAc nucleotide (UDP-GalNAc etc.) and GlcA nucleotide (UDP-GlcA etc.) as donor substrates to bind GalNAc to the non-reducing end of the acceptor substrate when the non-reducing end of the acceptor substrate is a GlcA residue, or bind GlcA to the non-reducing end of the acceptor substrate when the non-reducing end of the acceptor substrate is a GalNAc residue (Non-patent document 1, Patent document 1).

Although the concentration of K4CP is not particularly limited so long as sufficient activity of K4CP can be obtained, it is, for example, about 0.01 to 5000 μg/ml, preferably 0.1 to 500 μg/ml, more preferably 1 to 50 μg/ml, as the final concentration of K4CP in a reaction system.

The first method of the present invention comprises at least the step of allowing GlcA donor, GalNAC donor, saccharide acceptor, K4CP, and $Mn^{2+}$ at a final concentration of 0.02 to 100 mM to coexist, and performing a reaction thereof.

The meaning of the term "coexist" referred to herein is not particularly limited, so long as these donor molecules, saccharide acceptor molecule, $Mn^{2+}$ and K4CP molecule are brought into a state that they should contact with one another. For example, these may be allowed to coexist in a solution, or may be allowed to coexist by continuously bringing a solution containing the aforementioned donors and acceptor into contact with K4CP immobilized on a suitable solid phase (beads, ultrafiltration membrane, dialysis membrane etc.). Therefore, for example, a column type reactor, a membrane type reactor and so forth can also be employed. Moreover, as in the method disclosed in International Patent Publication WO00/27437, the enzymatic reaction can be carried out with the acceptor immobilized on a solid phase. Furthermore, a bioreactor which regenerates (synthesizes) the donors may also be combined.

The "reaction" performed in a state that they coexist means an enzymatic reaction catalyzed by K4CP. This reaction is not particularly limited, so long as it is performed under conditions of 20 to 40° C. and pH 6 to 8 for 0.5 minute to 4 hours.

Especially, the aforementioned reaction is preferably performed under conditions of 22 to 37° C. and pH 6.2 to 7.8 for 10 minutes to 3 hours, more preferably performed under conditions of 24 to 35° C. and pH 6.5 to 7.8 for 10 minutes to 2 hours, still more preferably performed under conditions of 26 to 35° C. and pH 6.8 to 7.6 for 10 minutes to 2 hours, further preferably performed under conditions of 28 to 32° C. and pH 7 to 7.5 for 10 minutes to 2 hours, particularly preferably performed under conditions of 28 to 32° C. and pH 7 to 7.5 for 10 minutes to 1 hour.

Above all, the aforementioned reaction is preferably performed under conditions of 20 to 40° C. and pH 6 to 8 for 0.5 to 4 hours, more preferably performed under conditions of 22 to 37° C. and pH 6.2 to 7.8 for 0.5 to 3 hours, still more preferably performed under conditions of 24 to 35° C. and pH 6.5 to 7.8 for 0.5 to 2 hours, further preferably performed under conditions of 26 to 35° C. and pH 6.8 to 7.6 for 0.5 to 2 hours, much more preferably performed under conditions of 28 to 32° C. and pH 7 to 7.5 for 0.5 to 2 hours, particularly preferably performed under conditions of 28 to 32° C. and pH 7 to 7.5 for 0.5 to 1 hour.

Further, the $Mn^{2+}$ concentration is preferably 0.02 to 35 mM, more preferably 0.2 to 35 mM, under the aforementioned conditions.

In particular, the concentration is preferably 5 to 35 mM, more preferably 10 to 30 mM, still more preferably 15 to 25 mM, particularly preferably 20 mM.

This reaction is preferably performed with maintaining the temperature and pH to be constant. In order to maintain pH to be constant, this reaction is preferably carried out in a buffer having a buffering action in that pH region.

By performing the step of allowing the aforementioned donors, acceptor, $Mn^{2+}$ and K4CP to coexist and performing a reaction thereof under such conditions, a fraction containing more than 50% of CH represented by the general formula (1) can be obtained.

$$(GlcA\text{-}GalNAc)_n \qquad (1)$$

(In the formula, - represents a glycosidic bond, and n represents an arbitrary integer)

Here, the expression of "containing more than 50% of CH represented by the general formula (1)" means that CH represented by the general formula (1) is contained in a molecular number exceeding 50% of the total molecular number of CH represented by the general formula (1) and CH represented by the general formula (2). That is, it is meant that CH represented by the general formula (1) is contained in the fraction in a molecular number larger than the molecular number of CH represented by the general formula (2) contained in the fraction.

$$GalNAc\text{-}(GlcA\text{-}GalNAc)_n \qquad (2)$$

(In the formula, - represents a glycosidic bond, and n represents an arbitrary integer)

Whether the fraction contains more than 50% of CH represented by the general formula (1) can be confirmed on the basis of peak intensities of CH represented by the general formula (1) and CH represented by the general formula (2) in an MALDI-TOF-MS spectrum of the obtained fraction. As for specific method therefor, see the examples described later.

The state of the "fraction" produced by the method of the present invention is not also particularly limited, and it may be in a state of solution, solid (powder, frozen solution etc.) or the like.

Moreover, it is sufficient that each method of the present invention should comprise at least the step defined in each method of the present invention, and each method may further comprise other steps. For example, the step of separating CH represented by the general formula (1) and CH represented by the general formula (2), the step of purifying only CH represented by the general formula (1), and so forth may be further included.

The method of the present invention may further comprises, after the step of allowing a GlcA donor, a GalNAC donor, a saccharide acceptor, K4CP, and $Mn^{2+}$ to coexist, and performing a reaction thereof under the predetermined temperature and pH condition for the predetermined time, the step of adding a GlcA donor and/or a GalNAc donor and reacting them under same conditions. With such a step, a fraction containing CH represented by the general formula (1) and (2) at a desired ratio can be more efficiently produced.

In the method of the present invention, "GlcA" and "GalNAc" are preferably D-glucuronic acid and D-N-acetylgalactosamine, respectively. Further, as for the glycosidic bonds included in the general formulas mentioned in the method of the present invention, the glycosidic bond between GlcA and GalNAc (GlcA-GalNAc) is preferably β1-3 linkage, and the glycosidic bond between GalNAc and GlcA (GalNAc-GlcA) is preferably β1-4 linkage.

Moreover, in the method of the present invention, "GlcA donor", "GalNAc donor", "saccharide acceptor", "$Mn^{2+}$" and "K4CP" as well as the meanings of the terms such as "coexist", "reaction", "fraction" etc. are the same as those mentioned above.

<2> Second Method of the Present Invention

The second method of the present invention is a method for producing a fraction containing more than 50% of CH represented by the general formula (1), which comprises at least the step of allowing a GlcA donor, a GalNAc donor, a saccharide acceptor, K4CP, and $Mn^{2+}$ at a final concentration of 0.02 to 100 mM to coexist, and performing a reaction thereof so that all of the following conditions should be satisfied.

$$(GlcA\text{-}GalNAc)_n \qquad (1)$$

$$GalNAc\text{-}(GlcA\text{-}GalNAc)_n \qquad (2)$$

(In the formulas, - represents a glycosidic bond, and n represents an arbitrary integer)

(Conditions)

Condition 1: A CH content ratio of a fraction produced by allowing the GlcA donor, the GalNAc donor, the saccharide acceptor, K4CP, and $Mn^{2+}$ at a final concentration of 0.02 to 100 mM to coexist, and performing a reaction thereof under conditions of 30° C. and pH 7.2 for 5 hours is defined to be X. The "CH content ratio" means a ratio of "molecular number of the CH represented by the general formula (1) "/" molecular number of the CH represented by the general formula (2)".

Condition 2: A reaction time providing the CH content ratio of X in a fraction produced when the reaction is performed under conditions of "arbitrary temperature and pH at which K4CP can act" instead of "30° C. and pH 7.2" of the condition 1 is defined to be Y.

Condition 3: The reaction is performed at the same temperature and pH as those of the condition 2 for a time shorter than Y.

The "GlcA donor", "GalNAc donor", "saccharide acceptor", "$Mn^{2+}$" and "K4CP" to be used in the second method of the present invention as well as meanings of the terms such as "coexist", "reaction" and "fraction" are the same as those mentioned in the explanations mentioned for the first method of the present invention.

The second method of the present invention comprises at least the step of allowing a GlcA donor, a GalNAc donor, a saccharide acceptor, K4CP, and $Mn^{2+}$ at a final concentration of 0.02 to 100 mM to coexist, and performing a reaction thereof so that all of the following conditions 1 to 3 should be satisfied. The conditions are explained below, respectively.

Condition 1: A CH content ratio of a fraction produced by allowing the GlcA donor, the GalNAc donor, the saccharide acceptor, K4CP, and $Mn^{2+}$ at a final concentration of 0.02 to 100 mM to coexist, and performing a reaction thereof under conditions of 30° C. and pH 7.2 for 5 hours is defined to be X. The "CH content ratio" means a ratio of "molecular number of the CH represented by the general formula (1) "/" molecular number of the CH represented by the general formula (2)".

The "molecular number of CH represented by the general formula (1)" and the "molecular number of CH represented by the general formula (2)" referred to herein can be analyzed on the basis of peak intensities of CH represented by the general formula (1) and CH represented by the general formula (2) in an MALDI-TOF-MS spectrum of the obtained fraction. Specific method thereof will be described later in the examples.

Condition 2: A reaction time providing the CH content ratio of X in a fraction produced when the reaction is performed under conditions of "arbitrary temperature and pH at which K4CP can act" instead of "30° C. and pH 7.2" of the condition 1 is defined to be Y.

For example, it is assumed that "the arbitrary temperature and pH at which K4CP acts" are set to be "35° C. and pH 7.0", and when the reaction is performed by allowing the GlcA donor, the GalNAc donor, the saccharide acceptor, K4CP, and $Mn^{2+}$ at a final concentration of 20 mM to coexist, and performing a reaction thereof under conditions of 30° C. and pH 7.2 for 5 hours, the CH content ratio (X) of the produced fraction is 0.5. In this case, the reaction time Y can be determined so that it should provides a CH content ratio of 0.5 in a fraction produced by allowing the GlcA donor, the GalNAc donor, the saccharide acceptor, K4CP, and $Mn^{2+}$ at a final concentration of 20 mM to coexist, and performing a reaction thereof under conditions of 35° C. and pH 7.0.

Condition 3: The reaction is performed at the same temperature and pH as those of the condition 2 for a time shorter than Y.

For example, in the aforementioned example, when the reaction time (Y) is 2.5 hours for providing a CH content ratio (X) of 0.5 in the fraction produced by allowing the GlcA donor, the GalNAc donor, the saccharide acceptor, K4CP, and $Mn^{2+}$ at a final concentration of 20 mM to coexist, and performing a reaction thereof under the conditions of 35° C. and pH 7.0, a fraction containing more than 50% of CH represented by the general formula (1) can be produced by allowing the GlcA donor, the GalNAc donor, the saccharide acceptor, K4CP, and $Mn^{2+}$ at a final concentration of 20 mM to coexist, and performing a reaction thereof under the conditions of 35° C. and pH 7.0 for a time shorter than 2.5 hours.

More specifically, the reaction is performed for a time, for example, 10 minutes to 2.4 hours shorter, preferably 30 minutes to 2.2 hours shorter, more preferably 1 to 2 hours shorter than Y.

The meaning of "containing more than 50% of CH represented by the general formula (1)" and the method for confirming whether the fraction contains more than 50% of CH represented by the general formula (1) may be the same as those mentioned in the explanations for the aforementioned first method of the present invention.

The $Mn^{2+}$ concentration is preferably 5 to 100 mM, more preferably 10 to 30 mM, still more preferably 15 to 25 mM, particularly preferably 20 mM, under the aforementioned conditions.

<3> Third Method of the Present Invention

The third method of the present invention is a method for producing a fraction containing more than 50% of CH represented by the general formula (2), which comprises at least the step of allowing a GlcA donor, a GalNAc donor, a saccharide acceptor, K4CP, and $Mn^{2+}$ at a final concentration of 5 to 100 mM to coexist, and performing a reaction thereof under conditions of 20 to 40° C. and pH 6 to 8 for 10 hours or longer.

$$\text{GalNAc-(GlcA-GalNAc)}_n \quad (2)$$

(In the formula, - represents a glycosidic bond, and n represents an arbitrary integer)

The "GlcA donor", "GalNAc donor", "saccharide acceptor", "$Mn^{2+}$" and "K4CP" to be used in the third method of the present invention as well as meanings of the terms such as "coexist", "reaction" and "fraction" are the same as those mentioned in the explanations mentioned for the first method of the present invention.

The expression of "containing more than 50% of CH represented by the general formula (2)" means that CH represented by the general formula (2) is contained in a molecular number exceeding 50% of the total molecular number of CH represented by the general formula (2) and CH represented by the general formula (1). That is, it is meant that CH represented by the general formula (2) is contained in the fraction in a molecular number larger than the molecular number of CH represented by the general formula (1) contained in the fraction.

$$(\text{GlcA-GalNAc})_n \quad (1)$$

(In the formula, - represents a glycosidic bond, and n represents an arbitrary integer)

The method for confirming whether the fraction contains more than 50% of CH represented by the general formula (2) is the same as that mentioned in the explanations for the aforementioned first method of the present invention.

Reaction conditions for the reaction of the third method of the present invention are not particularly limited so long as the reaction is performed under the conditions of 20 to 40° C. and pH 6 to 8 for 10 hours or longer. Especially, the aforementioned reaction is preferably performed under conditions of 22 to 37° C. and pH 6.2 to 7.8 for 10 to 30 hours, more preferably performed under conditions of 24 to 35° C. and pH 6.5 to 7.8 for 12 to 24 hours, still more preferably performed under conditions of 26 to 35° C. and pH 6.8 to 7.6 for 12 to 24 hours, further preferably performed under conditions of 28 to 32° C. and pH 7 to 7.5 for 12 to 24 hours, particularly preferably performed under conditions of 28 to 32° C. and pH 7 to 7.5 for 15 to 20 hours.

Further, the Mn²⁺ concentration is preferably 5 to 35 mM, more preferably 10 to 30 mM, still more preferably 15 to 25 mM, particularly preferably 20 mM, under the aforementioned conditions.

This reaction is preferably performed with maintaining the temperature and pH to be constant. In order to maintain pH to be constant, this reaction is preferably carried out in a buffer having a buffering action in that pH region, as in the first method of the present invention.

<4> Fourth Method of the Present Invention

The fourth method of the present invention is a method for producing a fraction containing more than 50% of CH represented by the general formula (2), which comprises at least the step of allowing a GlcA donor, a GalNAc donor, a saccharide acceptor, K4CP, and Mn²⁺ at a final concentration of 5 to 100 mM to coexist, and performing a reaction thereof so that all of the following conditions 4 to 6 should be satisfied.

$$(GlcA\text{-}GalNAc)_n \qquad (1)$$

$$GalNAc\text{-}(GlcA\text{-}GalNAc)_n \qquad (2)$$

(In the formulas, - represents a glycosidic bond, and n represents an arbitrary integer)
(Conditions)
Condition 4: A CH content ratio of a fraction produced by allowing the GlcA donor, the GalNAc donor, the saccharide acceptor, K4CP, and Mn²⁺ at a final concentration of 5 to 100 mM to coexist, and performing a reaction thereof under conditions of 30° C. and pH 7.2 for 8 hours is defined to be X. The "CH content ratio" mentioned above means a ratio of "molecular number of the CH represented by the general formula (1) "/" molecular number of the CH represented by the general formula (2)".

Conditions 5: A reaction time providing the CH content ratio of X in a fraction produced when the reaction is performed under conditions of "arbitrary temperature and pH at which K4CP can act" instead of "30° C. and pH 7.2" of the condition 4 is defined to be Y.

Condition 6: The reaction is performed at the same temperature and pH as those of the condition 5 for a time longer than Y.

The "GlcA donor", "GalNAc donor", "saccharide acceptor", "Mn²⁺" and "K4CP" to be used in the fourth method of the present invention as well as meanings of the terms such as "coexist", "reaction" and "fraction" are the same as those mentioned in the explanations mentioned for the first method of the present invention.

The fourth method of the present invention comprises at least the step of allowing a GlcA donor, a GalNAc donor, a saccharide acceptor, K4CP, and Mn²⁺ at a final concentration of 5 to 100 mM to coexist, and performing a reaction thereof so that all of the following conditions should be satisfied. The conditions are explained below, respectively.

Condition 4: A CH content ratio of a fraction produced by allowing the GlcA donor, the GalNAc donor, the saccharide acceptor, K4CP, and Mn²⁺ at a final concentration of 5 to 100 mM to coexist, and performing a reaction thereof under conditions of 30° C. and pH 7.2 for 8 hours is defined to be X. The "CH content ratio" mentioned above means a ratio of "molecular number of the CH represented by the general formula (1) "/" molecular number of the CH represented by the general formula (2)".

The "molecular number of CH represented by the general formula (1)" and the "molecular number of CH represented by the general formula (2)" referred to herein can be confirmed in the same manner as that described for the aforementioned second method of the present invention.

Conditions 5: A reaction time providing the CH content ratio of X in a fraction produced when the reaction is performed under conditions of "arbitrary temperature and pH at which K4CP can act" instead of "30° C. and pH 7.2" of the condition 4 is defined to be Y.

For example, it is assumed that "the arbitrary temperature and pH at which K4CP acts" are set to be "35° C. and pH 7.0", and when the reaction is performed by allowing the GlcA donor, the GalNAc donor, the saccharide acceptor, K4CP, and Mn²⁺ at a final concentration of 20 mM to coexist, and performing a reaction thereof under the condition of 30° C. and pH 7.2 for 8 hours, the CH content ratio (X) is 0.5. In this case, the reaction time Y can be determined so that it should provides a CH content ratio of 0.5 in a fraction produced by allowing the GlcA donor, the GalNAc donor, the saccharide acceptor, K4CP, and Mn²⁺ at a final concentration of 20 mM to coexist, and performing a reaction thereof under conditions of 35° C. and pH 7.0.

Condition 6: The reaction is performed at the same temperature and pH as those of the condition 5 for a time longer than Y.

For example, in the aforementioned example, when the reaction time (Y) is 6 hours for providing a CH content ratio (X) of 0.5 in the fraction produced by allowing the GlcA donor, the GalNAc donor, the saccharide acceptor, K4CP, and Mn²⁺ at a final concentration of 20 mM to coexist, and performing a reaction thereof under the conditions of 35° C. and pH 7.0, a fraction containing more than 50% of CH represented by the general formula (2) can be produced by allowing the GlcA donor, the GalNAc donor, the saccharide acceptor, K4CP, and Mn²⁺ at a final concentration of 20 mM to coexist, and . performing a reaction thereof under the conditions of 35° C. and pH 7.0 for a time longer than 6 hours.

More specifically, the reaction is performed for a time, for example, 4 to 24 hours longer, preferably 5 to 21 hours longer, more preferably 6 to 18 hours longer than Y.

The meaning of "containing more than 50% of CH represented by the general formula (2)" and the method for confirming whether the fraction contains more than 50% of CH represented by the general formula (2) is the same as those mentioned in the explanations for the aforementioned third method of the present invention.

The Mn²⁺ concentration is preferably 5 to 35 mM, more preferably 10 to 30 mM, still more preferably 15 to 25 mM, particularly preferably 20 mM, under the aforementioned conditions.

<5> Fifth Method of the Present Invention

The fifth method of the present invention is a method for producing a fraction containing substantially 100% of CH represented by the general formula (1), which comprises at least the step of allowing a GlcA donor, a saccharide acceptor, K4CP, and Mn²⁺ at a final concentration of 0.02 to 100 mM to coexist, and performing a reaction thereof so that all of the following conditions A to C should be satisfied.

$$(GlcA\text{-}GalNAc)_n \qquad (1)$$

$$GalNAc\text{-}(GlcA\text{-}GalNAc)_n \qquad (2)$$

(In the formulas, - represents a glycosidic bond, and n represents an arbitrary integer)
(Conditions)
Condition A: A CH content ratio of a fraction produced by allowing the GlcA donor, the saccharide acceptor, K4CP, and Mn²⁺ at a final concentration of 0.02 to 100 mM to coexist, and performing a reaction thereof under conditions of 30° C. and pH 7.2 for 0.5 hour is defined to be X. The "CH content ratio" mentioned above means a ratio of "molecular number of the CH represented by the general formula (1) "/" molecular number of the CH represented by the general formula (2)".
Conditions B: A reaction time providing the CH content ratio of X in a fraction produced when the reaction is performed under conditions of "arbitrary temperature and pH at which K4CP can act" instead of "30° C. and pH 7.2" of the condition 1 is defined to be Y.
Condition C: The reaction is performed at the same temperature and pH as those of the condition B for a time longer than Y.

The $Mn^{2+}$ concentration is preferably 5 to 100 mM, more preferably 10 to 30 mM, still more preferably 15 to 25 mM, particularly preferably 20 mM, under the aforementioned conditions.

The "containing substantially 100% of certain CH" used in this application document means that when the fraction is analyzed by MALDI-TOF-MS to obtain a spectrum, only peaks corresponding to a certain CH are observed, and peaks corresponding to other CH are not observed. For example, the expression "containing substantially 100% of CH represented by the general formula (1)" means that only the peaks of CH represented by the general formula (1) are observed, and the peaks of CH represented by the general formula (2) are not observed.

The "GlcA donor", "saccharide acceptor", "$Mn^{2+}$" and "K4CP" to be used in the fifth method of the present invention as well as meanings of the terms such as "coexist", "reaction" and "fraction" are the same as those mentioned in the explanations mentioned for the first method of the present invention. However, the "saccharide acceptor" used in the fifth method of the present invention preferably consists of a mixture of the saccharide chains represented by the general formulas (3) or (4). Examples of such a mixture include a fraction of CH molecules having different non-reducing end structures, a fraction of CH molecules obtained by chemical desulfation of a fraction of CS molecules having different non-reducing end structures, a fraction of CH molecules having different non-reducing end structures produced with a CH synthetase such as K4CP, and so forth.

The meanings of the terms and so forth used in the condition A to C are the same as those mentioned above.

In the fifth method of the present invention, the "time longer than Y" is, specifically, a time, for example, 10 minutes to 24 hours longer, preferably 30 minutes to 18 hours longer, more preferably 30 minutes to 5 hours longer than Y.

<6> Sixth Method of the Present Invention

The sixth method of the present invention is a method for producing a fraction containing substantially 100% of CH represented by the general formula (2), which comprises at least the step of allowing a GalNAc donor, a saccharide acceptor, K4CP, and $Mn^{2+}$ at a final concentration of 0.02 to 100 mM to coexist, and performing a reaction thereof so that all of the following conditions D to F should be satisfied.

(1)

(2)

(In the formulas, - represents a glycosidic bond, and n represents an arbitrary integer)
(Conditions)
Condition D: A CH content ratio of a fraction produced by allowing the GalNAc donor, the saccharide acceptor, K4CP, and $Mn^{2+}$ at a final concentration of 0.02 to 100 mM to coexist, and performing a reaction thereof under conditions of 30° C. and pH 7.2 for 0.5 hour is defined to be X. The "CH content ratio" mentioned above means a ratio of "molecular number of the CH represented by the general formula (1) "/" molecular number of the CH represented by the general formula (2)".
Conditions E: A reaction time providing the CH content ratio of X in a fraction produced by performing the reaction under conditions of "arbitrary temperature and pH at which K4CP can act" instead of "30° C. and pH 7.2" of the condition D is defined to be Y.
Condition F: The reaction is performed at the same temperature and pH as those of the condition E for a time longer than Y.

The $Mn^{2+}$ concentration is preferably 5 to 100 mM, more preferably 10 to 30 mM, still more preferably 15 to 25 mM, particularly preferably 20 mM, under the aforementioned conditions.

The "GalNAc donor", "saccharide acceptor", "$Mn^{2+}$" and "K4CP" to be used in the sixth method of the present invention as well as meanings of the terms such as "coexist", "reaction" and "fraction" are the same as those mentioned in the explanations mentioned for the first method of the present invention. However, the "saccharide acceptor" used in the sixth method of the present invention preferably consists of a mixture of the saccharide chains represented by the general formulas (3) and (4). Examples of such a mixture include a fraction of CH molecules having different non-reducing end structures, a fraction of CH molecules obtained by chemical desulfation of a fraction of CS molecules having different non-reducing end structures, a fraction of CH molecules having different non-reducing end structures produced with a CH synthetase such as K4CP, and so forth.

The meanings of the terms and so forth used in the condition D to F are the same as those mentioned above.

In the sixth method of the present invention, the "time longer than Y" is, specifically, a time, for example, 10 minutes to 24 hours longer, preferably 30 minutes to 18 hours longer, more preferably 30 minutes to 5 hours longer than Y.

<7> Seventh Method of the Present Invention

The seventh method of the present invention is a method for producing a fraction containing CH represented by the general formulas (1) and (2) at a content ratio ((1):(2)) of 45:55 to 55:45, which comprises at least the step of allowing a GlcA donor, a GalNAc donor, a saccharide acceptor, K4CP, and $Mn^{2+}$ at a final concentration of 0.02 to 2 mM to coexist, and performing a reaction thereof under conditions of 20 to 40° C. and pH 6 to 8 for 5 hours or longer.

(1)

(2)

(In the formulas, - represents a glycosidic bond, and n represents an arbitrary integer)

Reaction conditions for the reaction in the seventh method of the present invention are not particularly limited so long as the reaction is performed under the conditions of 20 to 40° C. and pH 6 to 8 for 5 hours or longer.

Especially, the aforementioned reaction is preferably performed under conditions of 22 to 37° C. and pH 6.2 to 7.8 for 10 to 30 hours, more preferably performed under conditions of 24 to 35° C. and pH 6.5 to 7.8 for 12 to 24 hours, still more preferably performed under conditions of 26 to 35° C. and pH 6.8 to 7.6 for 12 to 24 hours, further preferably performed under conditions of 28 to 32° C. and pH 7 to 7.5 for 12 to 24 hours, particularly preferably performed under conditions of 28 to 32° C. and pH 7 to 7.5 for 15 to 18 hours.

Further, the $Mn^{2+}$ concentration is preferably 0.1 to 1 mM, more preferably 0.2 mM, under the aforementioned conditions.

This reaction is preferably performed with maintaining the temperature and pH to be constant. In order to maintain pH to be constant, this reaction is preferably carried out in a buffer having a buffering action in that pH region, as in the first method of the present invention.

The "GlcA donor", "GalNAc donor", "saccharide acceptor", "$Mn^{2+}$" and "K4CP" to be used in the seventh method of the present invention as well as meanings of the terms such as "coexist", "reaction" and "fraction" are the same as those mentioned in the explanations mentioned for the first method of the present invention.

<8> Eighth Method of the Present Invention

The eighth method of the present invention is a method for producing a fraction containing CH represented by the general formulas (1) and (2) at a desired content ratio, which comprises at least the step of allowing a GlcA donor and/or a GalNAc donor, a saccharide acceptor, K4CP, and $Mn^{2+}$ to coexist, and performing a reaction thereof under conditions of 20 to 40° C. and pH 6 to 8.

(GlcA-GalNAc)$_n$      (1)

GalNAc-(GlcA-GalNAc)$_n$      (2)

(In the formulas, - represents a glycosidic bond, and n represents an arbitrary integer)

As explained for the aforementioned first to seventh methods of the present invention, if the reaction time is changed in the reaction in which a GlcA donor and/or GalNAc donor, a saccharide acceptor, K4CP and $Mn^{2+}$ are allowed to coexist at constant reaction temperature and pH, the ratio of CH molecules represented by the general formulas (1) and (2) in the produced fraction changes. Therefore, a fraction comprising CH represented by the general formulas (1) and (2) at a desired ratio can be obtained by appropriately controlling the reaction time.

Specific reaction temperature, pH, concentrations of K4CP and $Mn^{2+}$ can be suitably selected within the ranges shown for the first to seventh methods of the present invention.

As for the specific procedure of the eighth method of the present invention, a GlcA donor and/or a GalNAc donor, and a saccharide acceptor are reacted at constant reaction temperature, pH, $Mn^{2+}$ concentration etc. for various reaction times, ratios of CH molecules represented by the general formula (1) and (2) in the produced fractions are determined, and the reaction can be performed for a reaction time providing the desired ratio.

Examples

Hereafter, the present invention will be explained in detail with reference to examples.

(1) Preparation of CH Fractions as MALDI-TOF-MS Samples

[A] mentioned below is a preparation example of CH fractions containing more than 50% of CH molecules represented by the general formula (1), which are even number saccharides, obtained with a reaction time of 0.5 hour or 1 hour. [B] mentioned below is a preparation example of CH fractions containing more than 50% of CH molecules represented by the general formula (2), which are odd number saccharides, obtained with a reaction time of 18 hours.

(Preparation of CH Hexasaccharide ($CH_6$))

CH obtained by chemical desulfation of CS (Seikagaku Corporation) was limitedly decomposed with ovine testis hyaluronidase (Sigma) to obtain oligosaccharides of even number saccharides having GlcA residues as the non-reducing ends. They were purified by gel filtration and with an ion exchange column, and fractions corresponding to CH hexasaccharide (CH6) were collected and lyophilized. This CH6 evidently consisted of hexasaccharides having GalNAc residues as the reducing ends and GlcA residues as the non-reducing ends in view of the characteristics of the hyaluronidase used.

[A] To an enzymatic reaction mixture (200 µl) containing CH6 (10 nmol) prepared above, UDP-GalNAc and UDP-GlcA (300 nmol each), 50 mM Tris-HCl buffer, pH 7.2, 20 mM $MnCl_2$ and 0.15 M NaCl, a K4CP enzyme solution (recombinant enzyme obtained according to the procedure of the example of Japanese Patent Laid-open Publication (KOKAI) No. 2003-199583; corresponding to 3.75 µg protein) was added. A reaction was performed at 30° C. for 0.5 hour or 1 hour, thermal inactivation was performed for 1 minute in boiling water, the reaction mixture was subjected to ethanol precipitation, and the residue was dissolved again in 50 µl of distilled water. The solution was subjected to gel filtration chromatography in a Superdex Peptide HR10/30 column using 0.2 M ammonium acetate as a developing buffer. The solution was loaded at a flow rate of 1 ml/minute, and fractions were collected every 1 minute (1 ml). The obtained fractions were lyophilized, and each of the lyophilized fractions was dissolved again in 10 µl of distilled water. To remove excessive cations such as $Na^+$, the solution was loaded on a small amount of Dowex 50 XW8 ($H^+$ form) gel to obtain a sample for MALDI-TOF-MS.

[B] The same reaction was performed for 18 hours, and the reaction mixture was treated in the same way.

(2) Analysis

Structural analysis of CH obtained in (1) was performed by MALDI-TOF-MS (AutoFlex, Bruker). The negative mode for detecting produced anions was used for the analysis, and the analysis was performed in the reflection mode for the low molecular weight region (1 to 4 kDa) and linear mode for the high molecular weight regions (3 to 10 kDa and 5 to 20 kDa).

(Preparation of Target)

The obtained sample in a volume of 1 µl (containing 20 to 100 pmole of CH) and 1 µl of a 10 mg/ml solution of DHB (2,5-dihydroxybenzoic acid) in water containing 50% acetonitrile were mixed, and 1 µl of the mixture was spotted on a target plate and immediately dried by blowing nitrogen gas.

Figure 2:
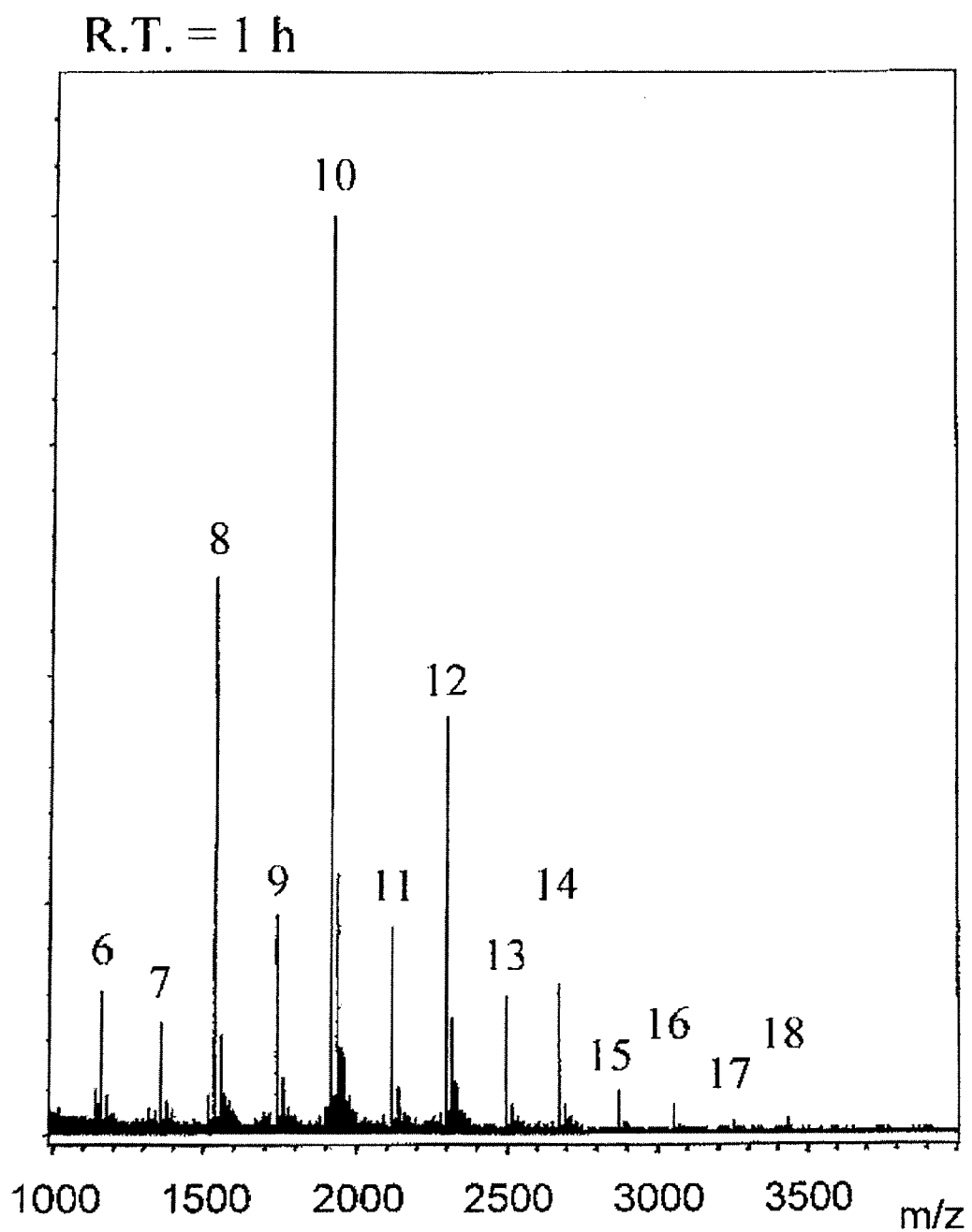
FIG. 2 MALDI-TOF-MS spectrum of a product obtained after the reaction for 1 hour.
Figure 3:
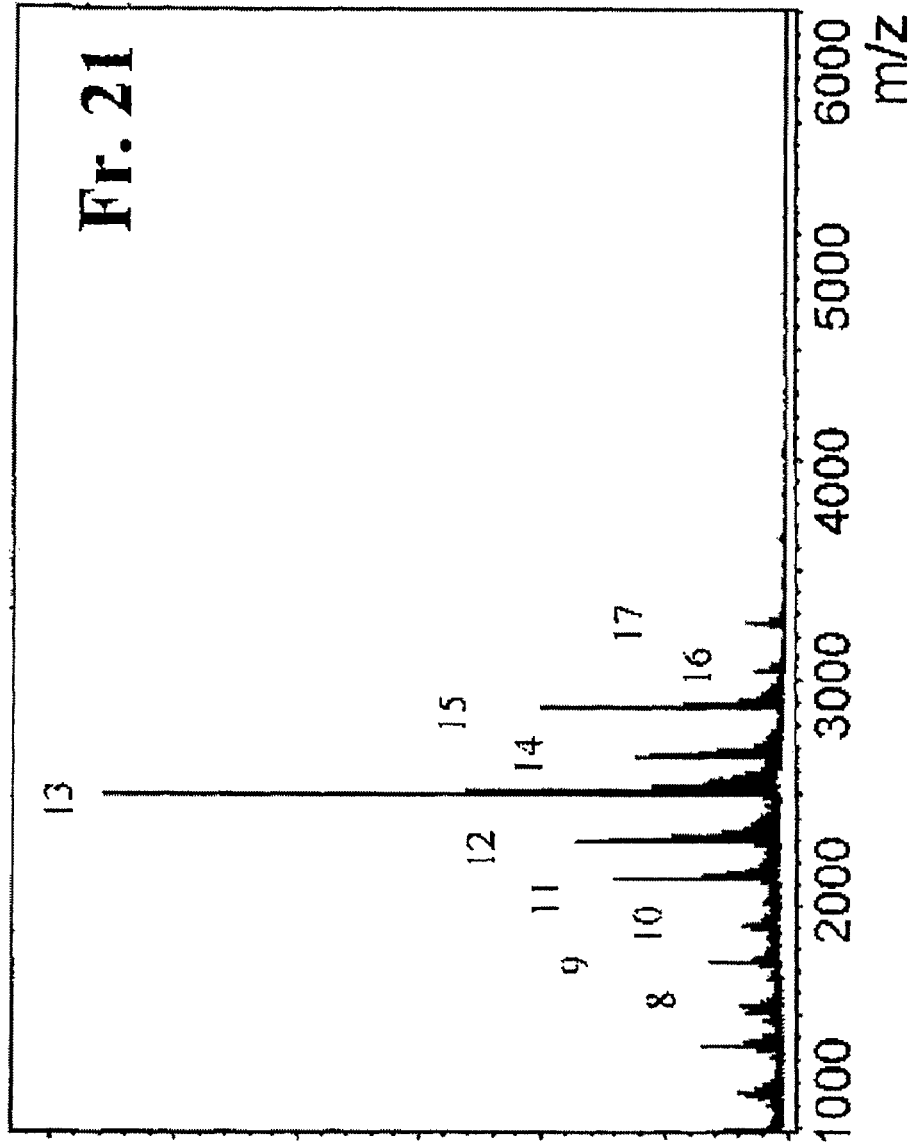
FIG. 3 MALDI-TOF-MS spectrum of an eluted fraction (fraction number 21) of a product obtained after the reaction for 18 hours.
Figure 4:
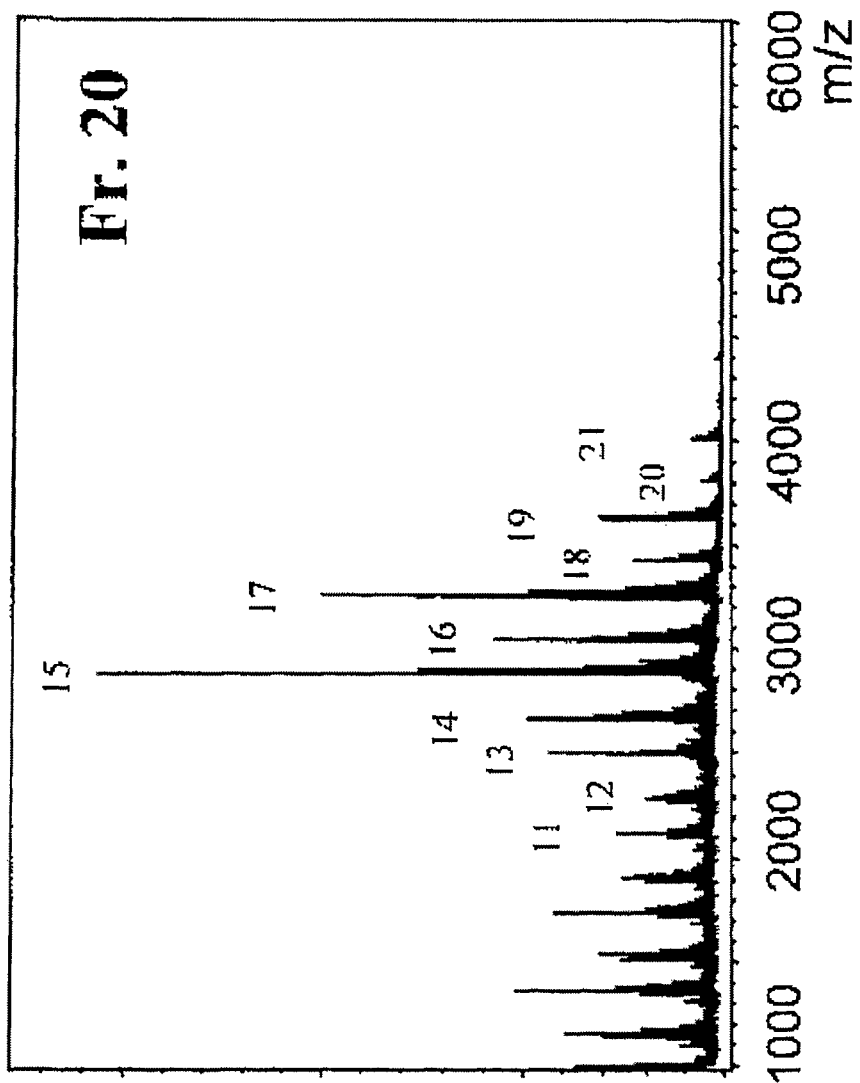
FIG. 4 MALDI-TOF-MS spectrum of an eluted fraction (fraction number 20) of a product obtained after the reaction for 18 hours.
Figure 5:
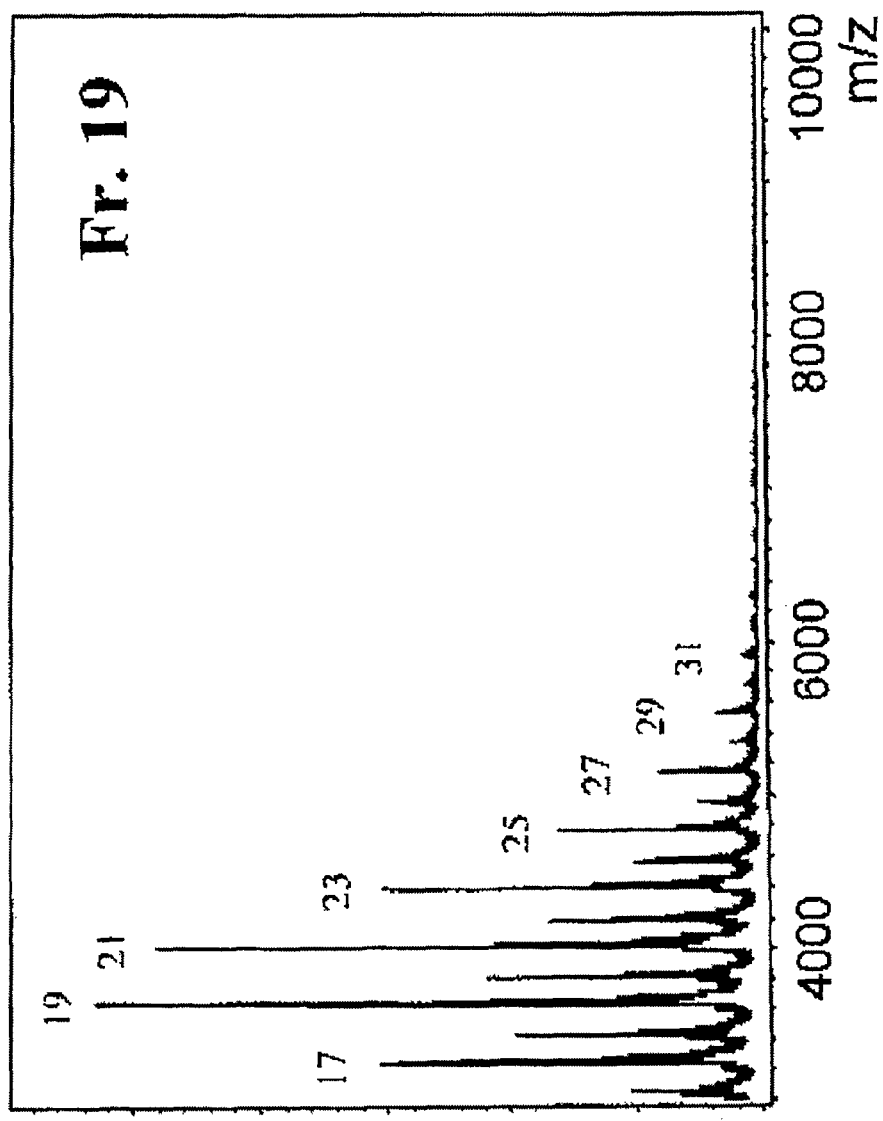
FIG. 5 MALDI-TOF-MS spectrum of an eluted fraction (fraction number 19) of a product obtained after the reaction for 18 hours.
Figure 6:
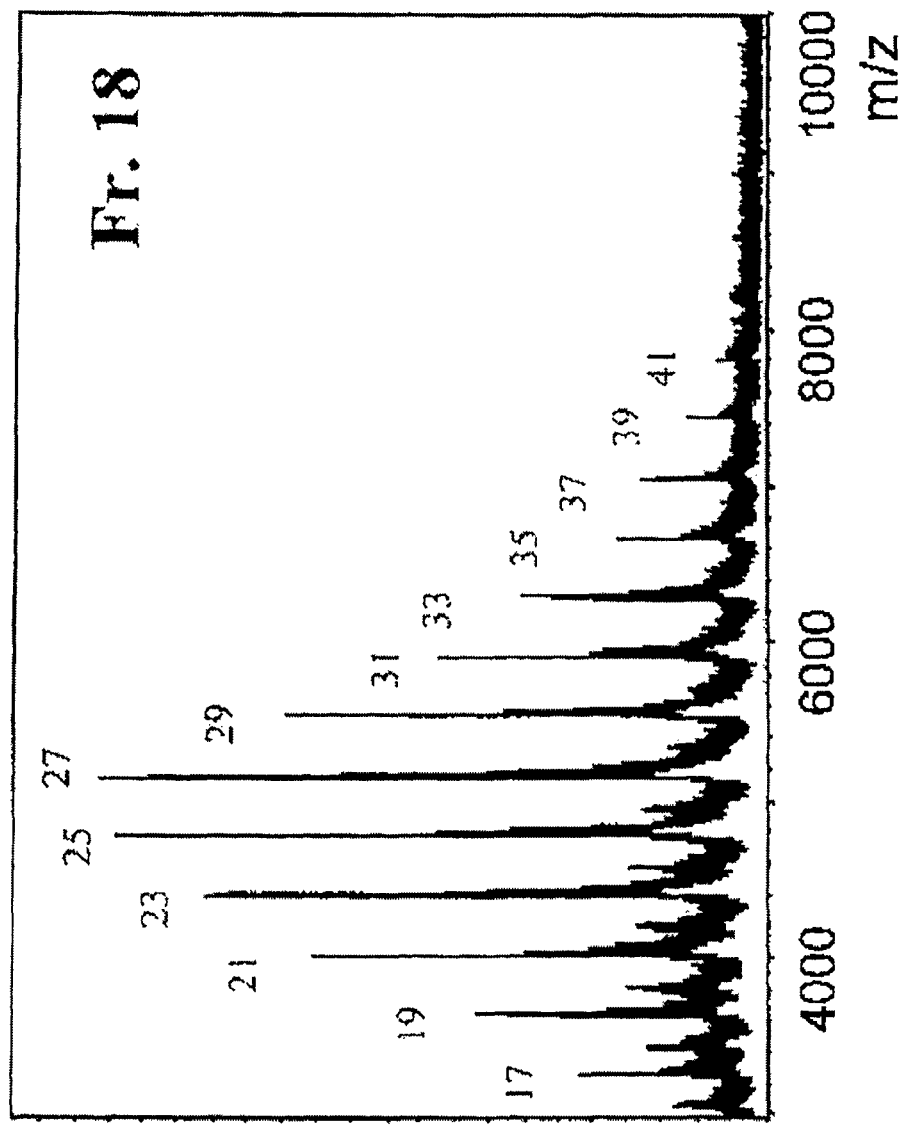
FIG. 6 MALDI-TOF-MS spectrum of an eluted fraction (fraction number 18) of a product obtained after the reaction for 18 hours.
Figure 7:
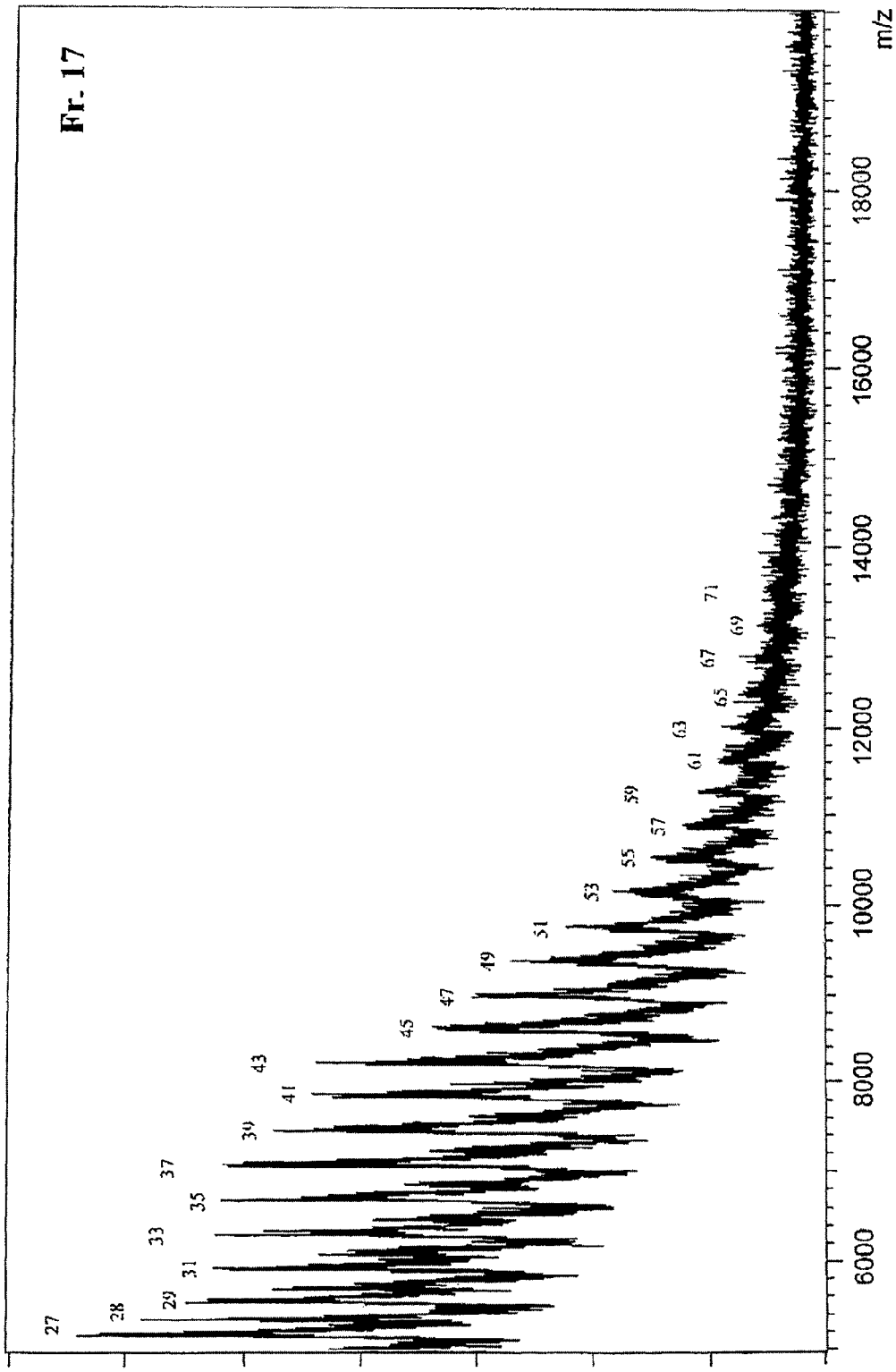
FIG. 7 MALDI-TOF-MS spectrum of an eluted fraction (fraction number 17) of a product obtained after the reaction for 18 hours.

(a) Analysis of Samples Obtained by Enzymatic Reaction for 0.5 Hour or 1 Hour by MALDI-TOF-MS The results of the analysis are shown in FIGS. 1 and 2, respectively. Since the saccharide chains produced by the reaction using CH6 as the acceptor substrate for a short period of time, 0.5 hour or 1 hour, were relatively low molecules, the measurement was performed in the reflection negative mode to scan a low molecular weight region (molecular weight range: 1,000 to 4,000) in the MALDI-TOF-MS analysis. In MALDI-TOF-MS, saccharide chain products having monosaccharide unit numbers increasing one by one were detected as definitely separated ion peaks, and the ion peak corresponding to CH decasaccharide (CH10, m/$z^-$=1912.56) was the highest. Comparison of the peaks of saccharide chains around that peak revealed that the peaks shifted to the higher molecular weight side in the sample obtained with the reaction time of 1 hour compared with the sample obtained with the reaction time of 0.5 hour. That is, it was found that the saccharide chains were extended with time course of the enzymatic reaction.

Further, the ion peaks of even number saccharides having GlcA residues as the non-reducing ends were higher than those of odd number saccharides having GalNAc residues as the non-reducing ends. Furthermore, relative intensities of the sum of values of ion peak intensities of the even number saccharides having GlcA residues as the non-reducing ends to the sum of values of ion peak intensities of the odd number saccharides having GalNAc residues as the non-reducing ends was 77.7:22.3 for the reaction of 0.5 hour, and 75.7:24.7 for the reaction of 1 hour. Thus, it is considered that the peak intensities and existence ratios of the molecules correlate with each other. Therefore, it was found that when the reaction was performed under the conditions of 30° C. and pH 7.2 for 0.5 hour or 1 hour, or under conditions equivalent thereto, the produced saccharide chain fraction predominantly contained (molecular number was larger) even number saccharides having GlcA residues as the non-reducing ends.

(b) Analysis of Samples Obtained by Enzymatic Reaction for 18 Hours by MALDI-TOF-MS The results of the analysis are shown in FIGS. 3 to 7. Among the fractions of the enzymatic reaction products eluted from a Superdex Peptide column, those of the fraction numbers 17 to 21 were analyzed by MALDI-TOF-MS. Since the samples of the fraction numbers 21 and 20 contained molecules having relatively low molecular weights, the measurement was performed in the reflection negative mode for a low molecular weight region of 1,000 to 6,000. As for the samples of the fraction numbers 19 and 18, the measurement was performed in the linear negative mode for a high molecular weight region (3,000 to 10,000). As for the sample of the fraction number 17, the measurement was performed in the linear negative mode for a further higher molecular weight region (5,000 to 20,000).

Each fraction showed continuous ion peaks of CH saccharide chains comprising the corresponding monosaccharide units increasing one by one, and the highest ion peaks were those of 13 saccharide ($m/z^-=2494.7$) for the fraction number 21, 15 saccharide ($m/z^-=2873.9$) for the fraction number 20, 19 saccharide ($m/z^-=3634.0$) for the fraction number 19, 27 saccharide ($m/z^-=5151.3$) for the fraction number 18, and 37 saccharide ($m/z^-=7047.9$) for the fraction number 17. In the MS spectrum of the sample of the fraction number 17, ion peaks of further higher molecular weights were observed, and ion peaks were identified for 71 saccharide ($m/z^-$=higher than 13,000) as the highest. Moreover, when the sum of the values of the ion peak intensities of the even number saccharides and the sum of the values of the odd number saccharides were compared, the ratios of the even number saccharides and the odd number saccharides were 14.6:85.4 in the fraction obtained in the elution time of from 17 to 18 minutes, and 29.1:70.9 in the fraction obtained in the elution time of from 15 to 16 minutes.

Therefore, it was found that when the reaction was performed under the conditions of 30° C. and pH 7.2 for a long period of time (18 hours), or under conditions equivalent thereto, odd number saccharides having GalNAc as the non-reducing ends became more dominant (molecular number became larger) in a longer chain region.

From the above results, it was revealed that, under the aforementioned conditions, a shorter reaction time provided a CH fraction in which even number saccharides were more dominant, and a longer reaction time provided a CH fraction in which odd number saccharides were more dominant.

(3)

(A) Preparation of Fractions of CH Having GalNAc Residues as Non-Reducing Ends

To an enzymatic reaction mixture (500 µl) containing CH obtained by chemical desulfation of CS and having different non-reducing ends (1 mg, average molecular weight: 10,000, Seikagaku Corporation), UDP-GalNAc (3 µmol) 50 mM Tris-HCl buffer, pH 7.2, 20 mM $MnCl_2$ and 0.15 M NaCl, a K4CP enzyme solution (recombinant enzyme obtained according to the procedure of the example of Japanese Patent Laid-open Publication (KOKAI) No. 2003-199583; corresponding to 37.5 µg protein) was added. A reaction was performed at 30° C. for 18 hours, thermal inactivation was performed for 1 minute in boiling water, the reaction mixture was subjected to ethanol precipitation, and the residue was dissolved again in 200 µl of distilled water. The solution was subjected to gel filtration chromatography in a Superdex 75 HR10/30 column using 0.2 M ammonium acetate as a developing buffer. The solution was loaded at a flow rate of 1 ml/minute, and fractions were collected every 1 minute (1 ml). The obtained fractions were lyophilized, and each of the lyophilized fractions was dissolved again in 10 µl of distilled water. From a part of the solution, 10 µl of a 1 nmole/µl solution was prepared, and the solution was loaded on a small amount of Dowex 50 XW8 ($H^+$ form) gel to prepare a sample for MALDI-TOF-MS.

(B) Preparation of Fractions of CH Having GlcA as Non-Reducing Ends

Saccharide chain fractions were prepared in the same manner as that of (A) except that UDP-GlcA was used instead of UDP-GalNAc to prepare sample solutions for MS.

(C) Analysis

Figure 8:
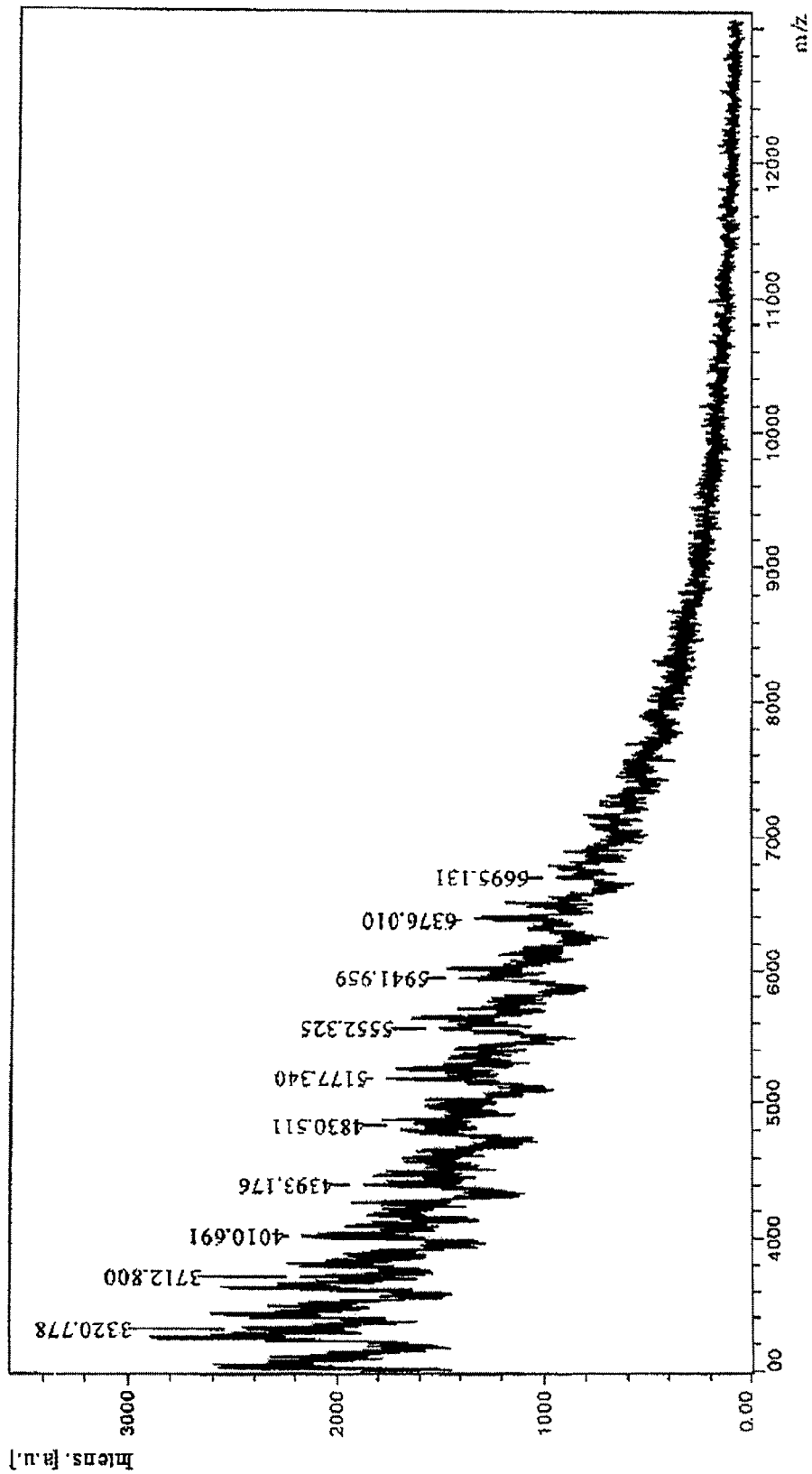
FIG. 8 MALDI-TOF-MS spectrum of a product obtained by the reaction of desulfated CS and a GalNAc donor.
Figure 9:
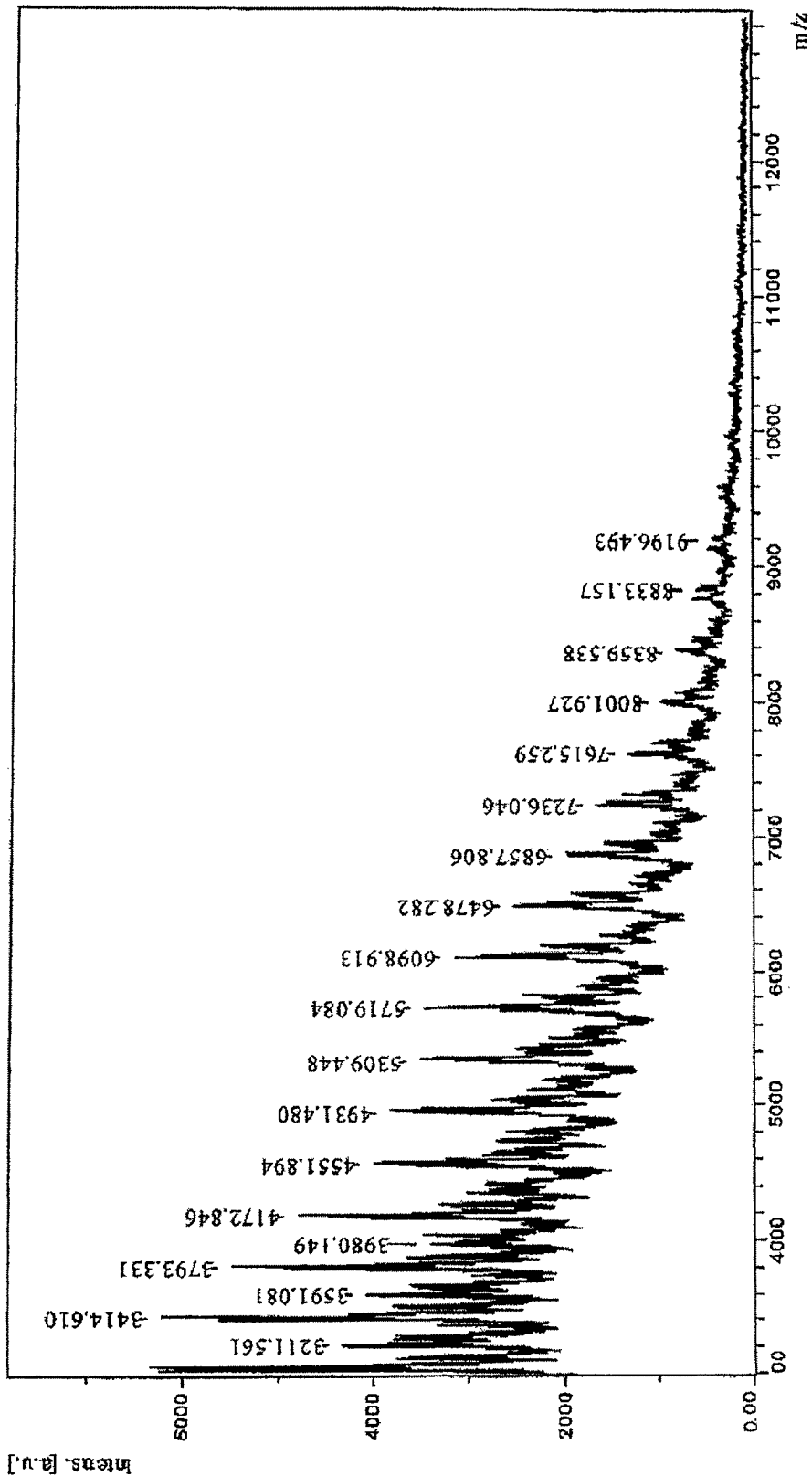
FIG. 9 MALDI-TOF-MS spectrum of a product obtained by the reaction of desulfated CS and a GlcA donor.

Mass spectrometry of the samples of (A) and (B) was performed in the same manner as that of (2) mentioned above. As a result, it was revealed on the basis of the m/z values of the ion peaks that substantially all the CH molecules in the fractions obtained in (A) were odd number saccharides having GalNAc as the non-reducing ends, and substantially all the CH molecules in the fractions obtained in (B) were even number saccharides having GlcA as the non-reducing ends (FIGS. 8 and 9).

(4)

(A) Preparation of Fractions of CH Having GalNAc as Non-Reducing Ends

A reaction was performed in the same manner as that of (1) mentioned above under conditions of 30° C. and pH 7.2 for 8 hours by using CH6, UDP-GalNAc and UDP-GlcA as substrates and adding the K4CP enzyme. Then, 300 nmole of UDP-GalNAc was added again, and the reaction was performed again at 30° C. for 5 hours. Thermal inactivation was performed for 1 minute in boiling water, the reaction mixture was subjected to ethanol precipitation, and the residue was dissolved again in 200 µl of distilled water. The solution was subjected to gel filtration chromatography in a Superdex Peptide HR10/30 column using 0.2 M ammonium acetate as a developing buffer. The mixture was loaded at a flow rate of 1 ml/minute, and fractions were collected every 1 minute (1 ml). The obtained fractions were lyophilized, and each of the lyophilized fractions was dissolved again in 10 µl of distilled water. The solution was loaded on a small amount of Dowex 50 XW8 ($H^+$ form) gel to obtain a sample for MALDI-TOF-MS.

(B) Preparation of Fractions of CH Having GlcA as Non-Reducing Ends

Saccharide chain fractions were prepared in the same manner as that of (A) except that UDP-GlcA was added again instead of UDP-GalNAc to prepare sample solutions for MS.

(C) Analysis

Figure 10:
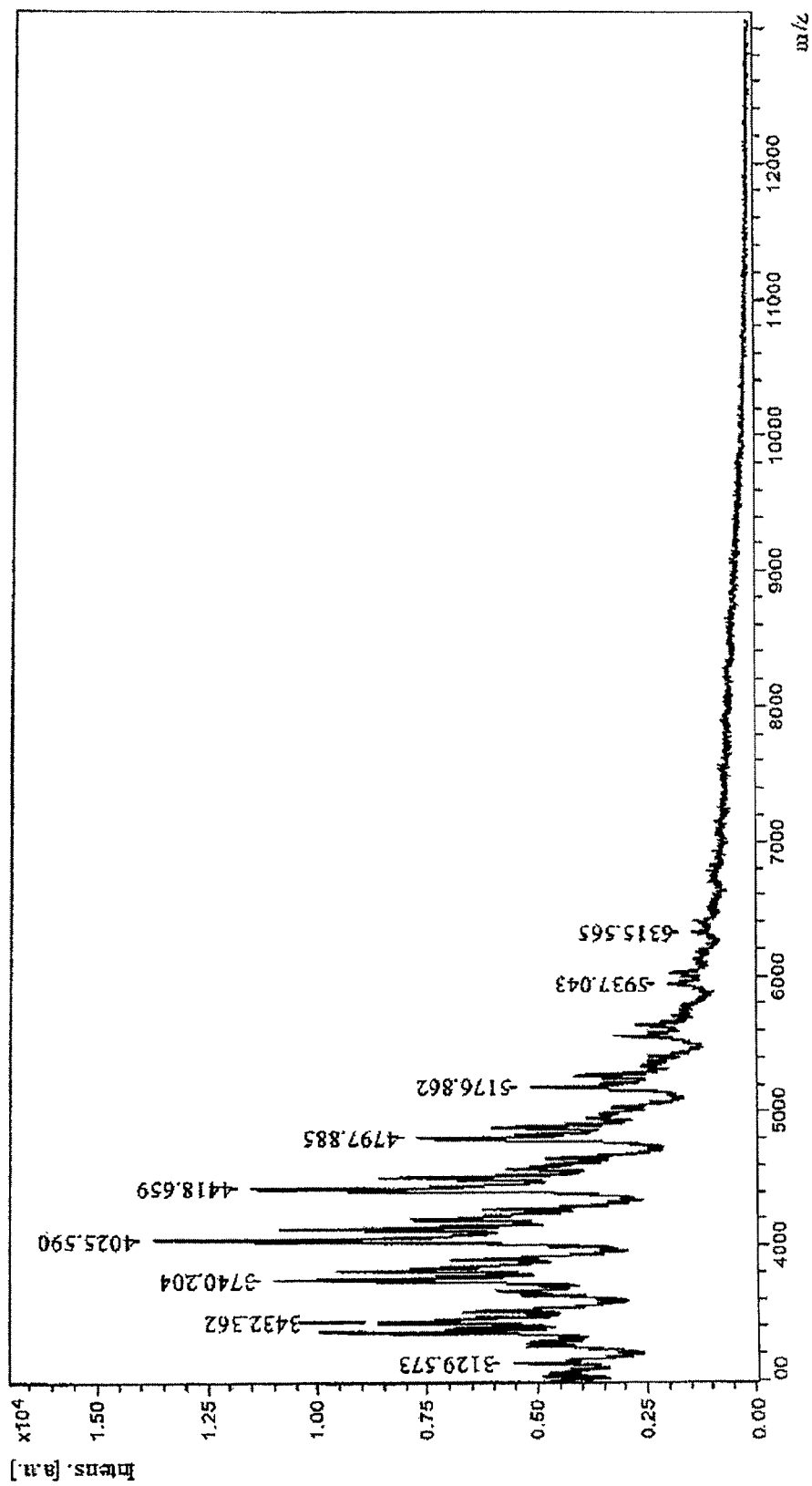
FIG. 10 MALDI-TOF-MS spectrum of a product obtained by the reaction of CH synthesized from CH6 and a GalNAc donor added again.
Figure 11:
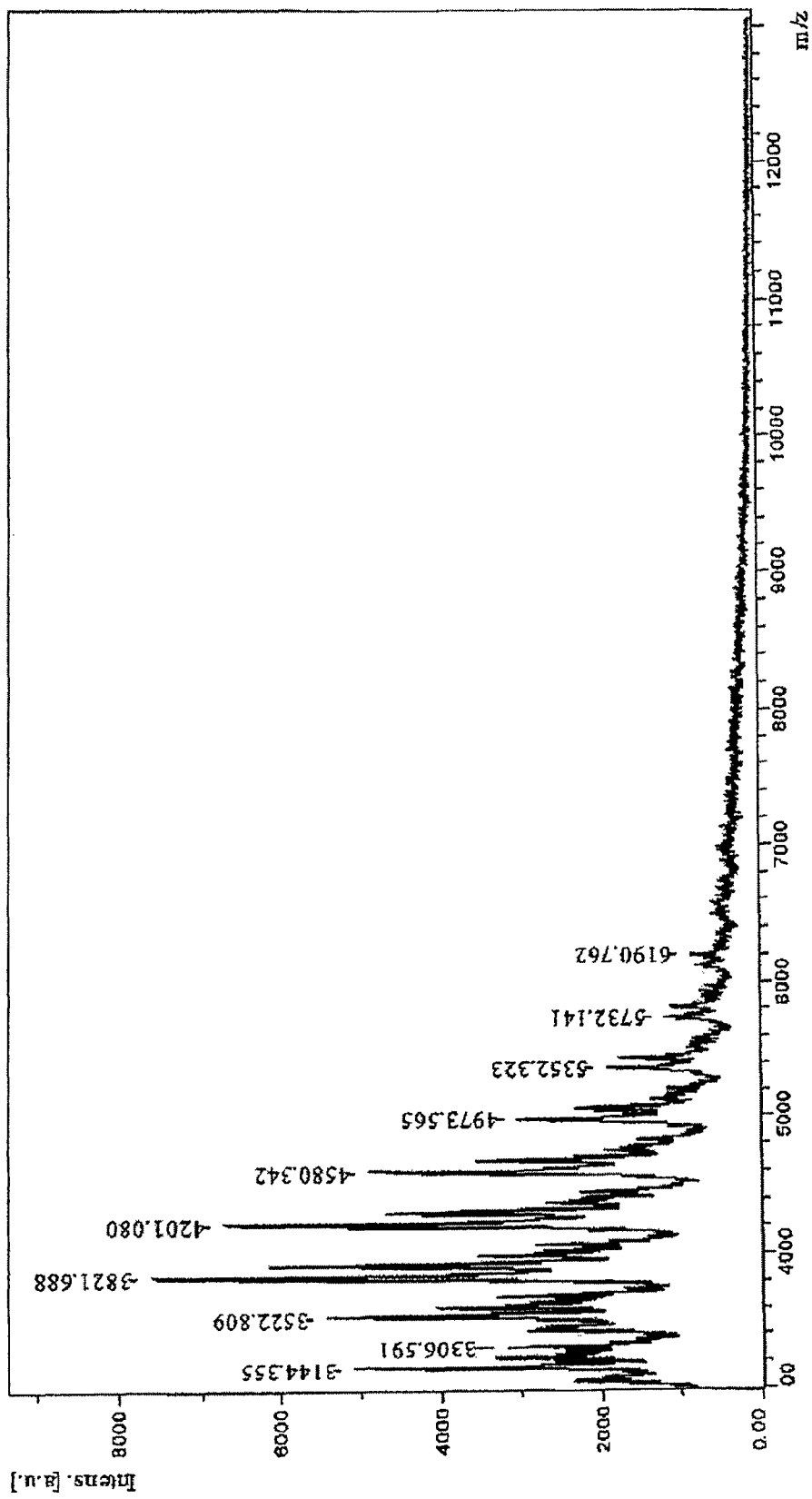
FIG. 11 MALDI-TOF-MS spectrum of a product obtained by the reaction of CH synthesized from CH6 and a GlcA donor added again.

Mass spectrometry of the samples of (A) and (B) was performed in the same manner as that of (2) mentioned above. As a result, it was revealed on the basis of the m/z values of the ion peaks that substantially all the CH molecules in the fraction obtained in (A) were odd number saccharides having GalNAc as the non-reducing ends, and substantially all the CH molecules in the fraction obtained in (B) were even number saccharides having GlcA as the non-reducing ends (FIGS. 10 and 11).

(5) Influence of $Mn^{2+}$ Concentration

Figure 12:
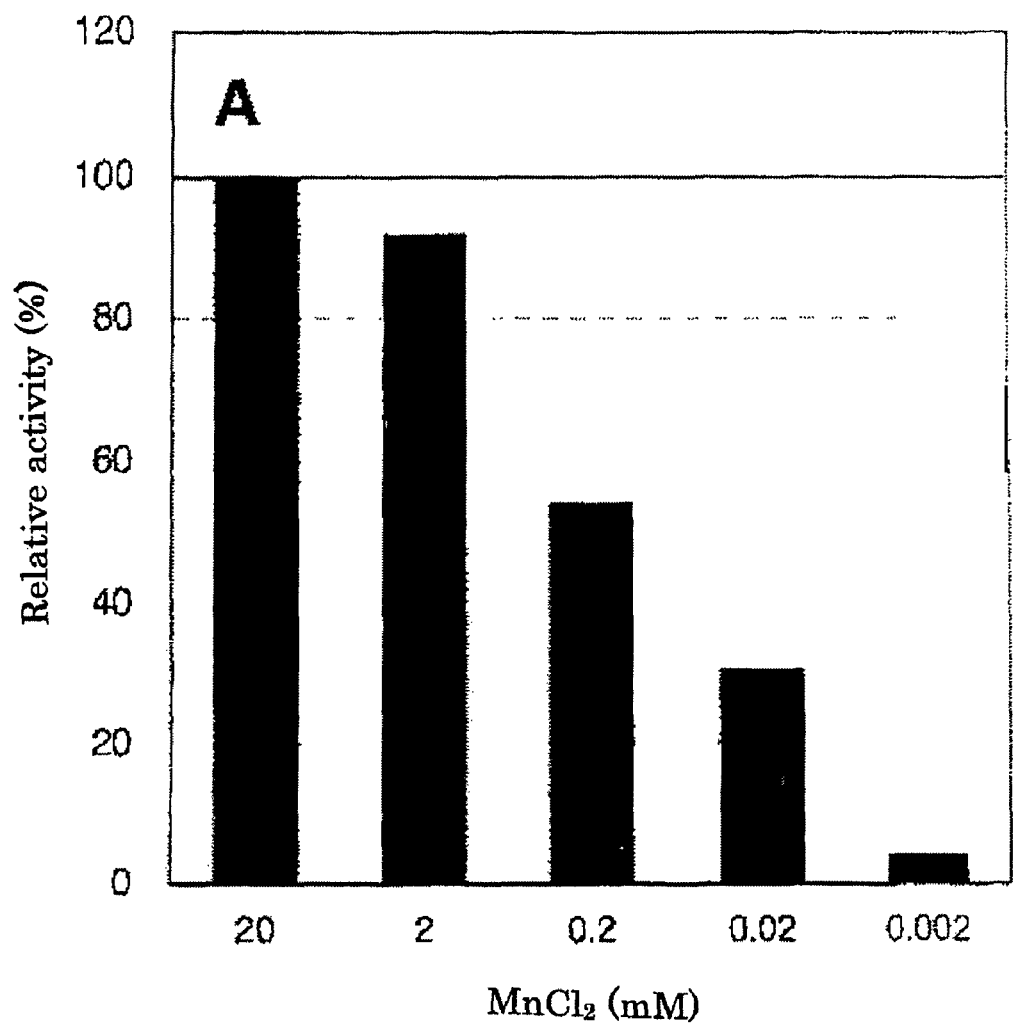
FIG. 12 Graph showing change of the enzymatic activity after the reaction for 0.5 hour, which was observed with changing the $Mn^{2+}$ concentration.
Figure 13:
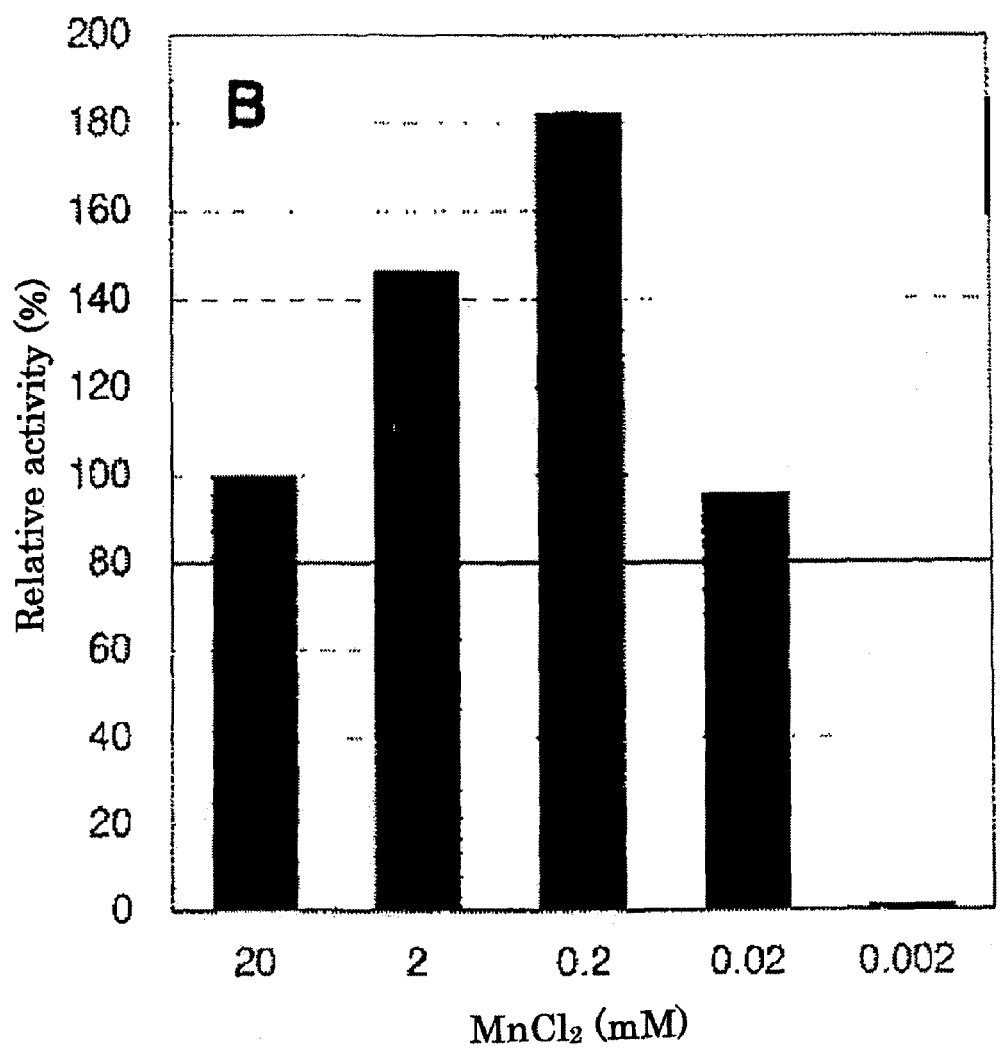
FIG. 13 Graph showing change of the enzymatic activity after the reaction for 18 hours, which was observed with changing the $Mn^{2+}$ concentration.

Influence of $Mn^{2+}$ on the K4CP enzyme reaction was examined. To a solution containing CH6 (10 nmol) prepared in Example 1, UDP-GalNAc and UDP-GlcA (300 nmol each), 50 mM Tris-HCl buffer, pH 7.2, and 0.15 M NaCl, $MnCl_2$ were added at a final concentration of 0.002, 0.02, 0.2, 2 and 20 mM to prepare enzymatic reaction solutions. To each enzymatic reaction solution (200 μl), a K4CP enzyme solution (corresponding to 3.75 μg of protein) was added. In the enzymatic reaction of 0.5 hour, the enzymatic activity (amount of produced CH) decreased with decrease of the $Mn^{2+}$ concentration (FIG. 12). Then, the $Mn^{2+}$ concentration dependency after 18 hours was investigated. Although the activity was considerably low at a $MnCl_2$ concentration of 0.002 mM, the enzymatic activity at 0.2 mM was about 1.8 times higher than that obtained with the concentration of 20 mM (FIG. 13).

Figure 14:
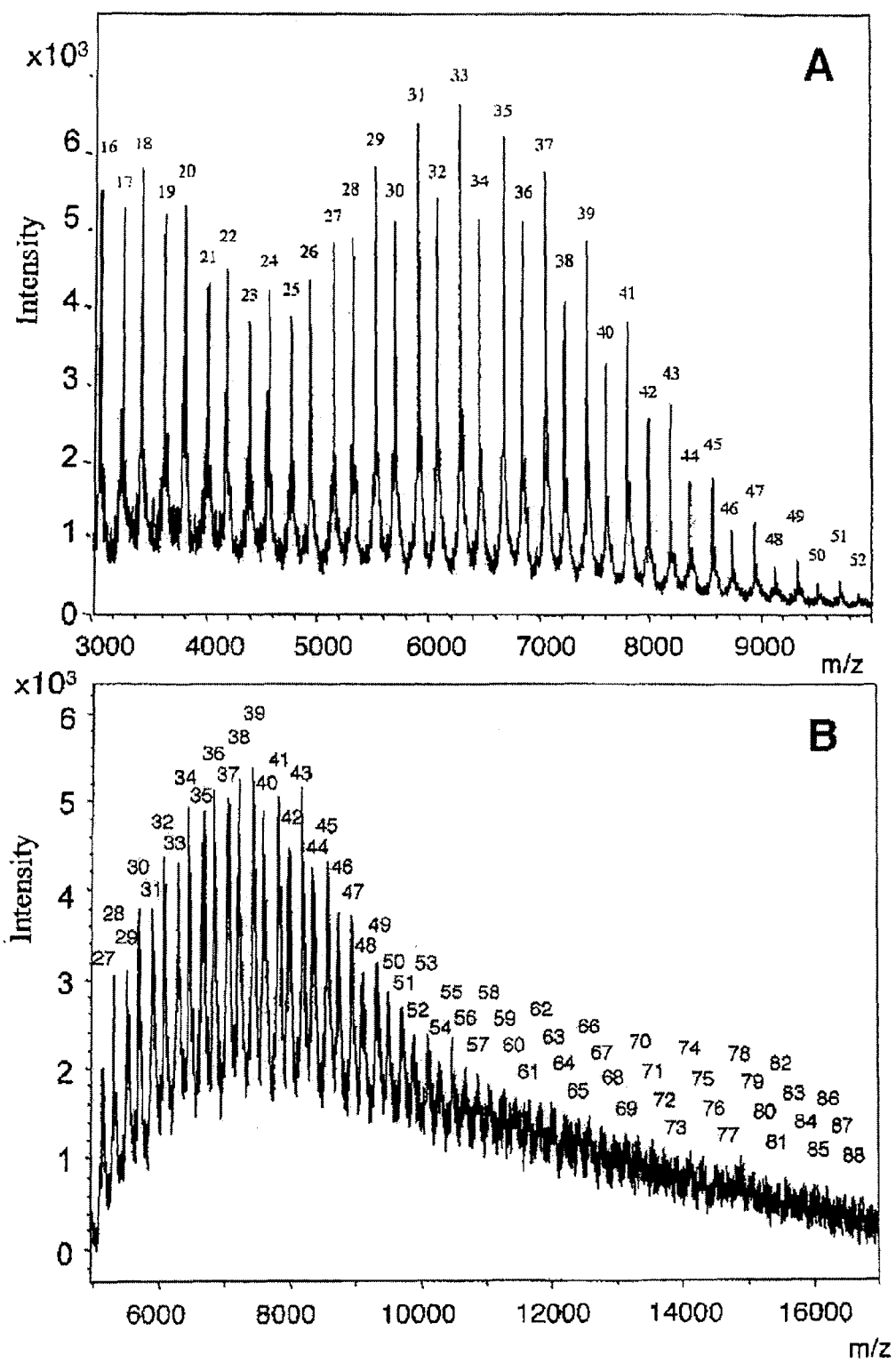
FIG. 14 MALDI-TOF-MS spectrum of a product obtained by the reaction for 18 hours at a $Mn^{2+}$ concentration of 0.2 mM.

Then, the reaction was performed for 18 hours in the reaction mixture containing 0.2 mM $MnCl_2$, the obtained product was subjected to gel filtration chromatography in a Superdex 75 HR10/30 column using 0.2 M ammonium acetate as a developing buffer. The product was loaded at a flow rate of 1 ml/minute, and fractions were collected every 1 minute (1 ml). The obtained fractions were lyophilized, and each of the lyophilized fractions was dissolved again in 10 μl of distilled water. From a part of the solution, 10 μl of a 1 nmole/μl solution was prepared, and the solution was loaded on a small amount of Dowex 50 XW8 ($H^+$ form) gel to obtain a sample for MALDI-TOF-MS. FIG. 14 (A) shows the results of MALDI-TOF-MS analysis of the fraction obtained in the elution time of from 17 to 18 minutes, and (B) shows the results of MALDI-TOF-MS analysis of the fraction obtained in the elution time of from 15 to 16 minutes. As seen from these results, by reducing the concentration of $MnCl_2$, the ratio of the even number saccharides and odd number saccharides was made substantially the same, and CH chains of higher molecular weights were produced (ion peak of 88 saccharides (m/z$^-$=16,752) were identified at most). Moreover, when the sum of the values of the ion peak intensities of the even number saccharides and the sum of the same of the odd number saccharides were compared, the ratios of the even number saccharides and the odd number saccharides were 48.5:51.5 in the fraction obtained in the elution time of from 17 to 18 minutes, and 49.0:51.0 in the fraction obtained in the elution time of from 15 to 16 minutes. Therefore, it was revealed that a fraction containing equivalent amounts of even number saccharides and odd number saccharides could be produced by adjusting the $Mn^{2+}$ concentration.

INDUSTRIAL APPLICABILITY

The method of the present invention can be used as a method for producing a fraction of CH of which non-reducing ends are controlled.

What is claimed is:

1. A method for producing a fraction comprising more than 50% of chondroitin represented formula (1), comprising the steps of:
   (a) reacting a glucuronic acid donor, a N-acetylgalactosamine donor, a saccharide acceptor, chondroitin polymerase derived from *Escherichia coli* K4, and $Mn^{2+}$ at a final concentration of 0.02 to 100 mM at 30° C. and pH 7.2 for 5 hours and measuring a chondroitin content ratio, X, in a fraction produced by the reaction, wherein the chondroitin content ratio, X, means a ratio of a number of chondroitin molecules represented by formula (1)/a number of chondroitin molecules represented by formula (2);
   (b) determining a reaction time for providing the chondroitin content ratio, X, as determined in step (a) in a fraction produced when the reaction is performed under conditions of arbitrary temperature and pH, other than at 30° C. and pH 7.2, at which the chondroitin polymerase derived from *Escherichia coli* K4 can act for a reaction time defined to be Y; and
   (c) performing the reaction at the same temperature and pH as step (b) for a time shorter than Y,
   wherein formulae (1) and (2) are:

$$(GlcA\text{-}GalNAc)_n \qquad (1)$$

$$GalNAc\text{-}(GlcA\text{-}GalNAc)_n \qquad (2)$$

wherein GlcA represents a glucuronic acid residue, GalNac represents an N-acetylgalactosamine residue, - represents a glycosidic bond and n represents an arbitrary integer.

2. A method for producing a fraction comprising more than 50% of chondroitin represented by formula (2), comprising the steps of:
   (a) reacting a glucuronic acid donor, a N-acetylgalactosamine donor, a saccharide acceptor, chondroitin polymerase derived from *Escherichia coli* K4, and $Mn^{2+}$ at a final concentration of 5 to 100 mM at 30° C. and pH 7.2 for 8 hours and measuring a chondroitin content ratio, X, in a fraction produced by the reaction, wherein the chondroitin content ratio, X, means a ratio of a number of chondroitin molecules represented by formula (1)/a number of chondroitin molecules represented by formula (2);
   (b) determining a reaction time for providing the chondroitin content ratio, X, as determined in step (a) in a fraction produced when the reaction is performed under conditions of arbitrary temperature and pH, other than at 30° C. and pH 7.2, at which the chondroitin polymerase derived from *Escherichia coli* K4 can act for a reaction time defined to be Y; and
   (c) performing the reaction at the same temperature and pH as step (b) for a time longer than Y,
   wherein formulae (1) and (2) are:

$$(GlcA\text{-}GalNAc)_n \qquad (1)$$

$$GalNAc\text{-}(GlcA\text{-}GalNAc)_n \qquad (2)$$

wherein, GlcA represents a glucuronic acid residue, GalNAc represents an N-acetylgalactosamine residue, - represents a glycosidic bond, and n represents an arbitrary integer.

* * * * *

UNITED STATES PATENT AND TRADEMARK OFFICE
CERTIFICATE OF CORRECTION

PATENT NO.      : 8,129,148 B2
APPLICATION NO. : 12/064810
DATED           : March 6, 2012
INVENTOR(S)     : Sugiura et al.

Page 1 of 1

It is certified that error appears in the above-identified patent and that said Letters Patent is hereby corrected as shown below:

Title page, item [57] line 6, Abstract, "receptor, a chondroitin" should be changed to
--acceptor, a chondroitin--

Title page, item [57] line 20, Abstract, "GalNACa represents" should be changed to
--GalNAc represents--

Column 2, line 48, "more than 500" should be changed to --more than 50%--

Column 4, line 44, "substantially 1000 of" should be changed to --substantially 100% of--

Column 4, line 65, "formula (2)":" should be changed to --formula (2)".--

Column 14, line 32, "coexist, and . performing" should be changed to --coexist, and performing--

Signed and Sealed this
Seventh Day of August, 2012

David J. Kappos
*Director of the United States Patent and Trademark Office*